US011045342B2

(12) United States Patent
Doyle

(10) Patent No.: US 11,045,342 B2
(45) Date of Patent: Jun. 29, 2021

(54) ADAPTIVE ARM SUPPORT SYSTEMS AND METHODS FOR USE

(71) Applicant: ENHANCE TECHNOLOGIES, LLC, San Diego, CA (US)

(72) Inventor: Mark C. Doyle, Del Mar, CA (US)

(73) Assignee: ENHANCE TECHNOLOGIES, LLC, San Diego, CA (US)

(*) Notice: Subject to any disclaimer, the term of this patent is extended or adjusted under 35 U.S.C. 154(b) by 294 days.

(21) Appl. No.: 16/011,577

(22) Filed: Jun. 18, 2018

(65) Prior Publication Data

US 2018/0360637 A1 Dec. 20, 2018

Related U.S. Application Data

(63) Continuation of application No. 13/563,728, filed on Jul. 31, 2012, now Pat. No. 9,999,534.

(51) Int. Cl.
*A61F 5/01* (2006.01)
*A61B 90/53* (2016.01)
*A61F 5/37* (2006.01)

(52) U.S. Cl.
CPC ............ *A61F 5/0118* (2013.01); *A61B 90/53* (2016.02); *A61F 5/3746* (2013.01)

(58) Field of Classification Search
CPC ...... A61B 90/53; A61B 90/60; A61H 1/0281; A61H 1/00; A61H 1/0274; A61F 5/013; A61F 5/0102; A61F 5/0118; A61F 5/3761; A61F 5/3769; A61F 5/3776; A61F 5/3792; A61F 2005/0134; A61F 2005/0197; A45F 2005/002; A41D 13/08; B25J 11/00; B25J 9/006; A63B 21/00; A63B 23/035

See application file for complete search history.

(56) References Cited

U.S. PATENT DOCUMENTS

| | | | | |
|---|---|---|---|---|
| 3,120,332 A | * | 2/1964 | White | A45B 11/02 224/189 |
| 5,020,521 A | * | 6/1991 | Salort | A61F 5/0118 602/20 |
| 2009/0259154 A1 | * | 10/2009 | Nace | A61F 5/0123 602/16 |

* cited by examiner

*Primary Examiner* — Christie L Bahena
(74) *Attorney, Agent, or Firm* — William A. English; Vista IP Law Group LLP

(57) ABSTRACT

Systems and methods are provided for supporting an arm of a user that includes a harness configured to be worn by the user, and an arm support coupled to the harness and including an arm rest to support an arm of the user. The arm support is configured to accommodate and follow movement of the arm without substantially interfering in such movement. The arm support may at least partially offset a gravitational force acting on the arm as the user moves and the arm support follows the movement of the user's arm. For example, the arm support may transfer at least a portion of the weight of the user's arm to the torso or other region of the user's body and/or may apply an opposing force to at least partially offset the gravitational force acting on the arm.

17 Claims, 24 Drawing Sheets

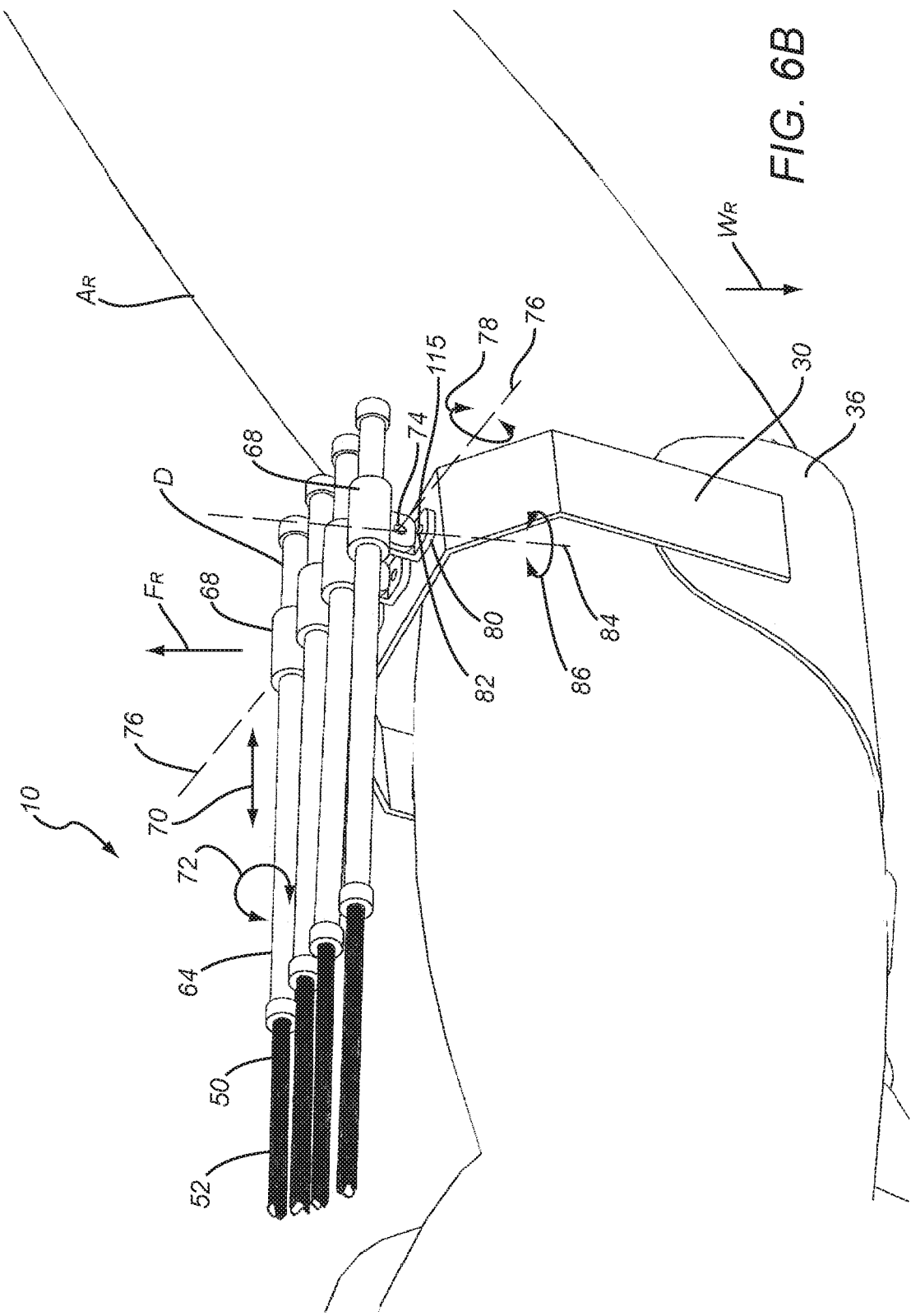

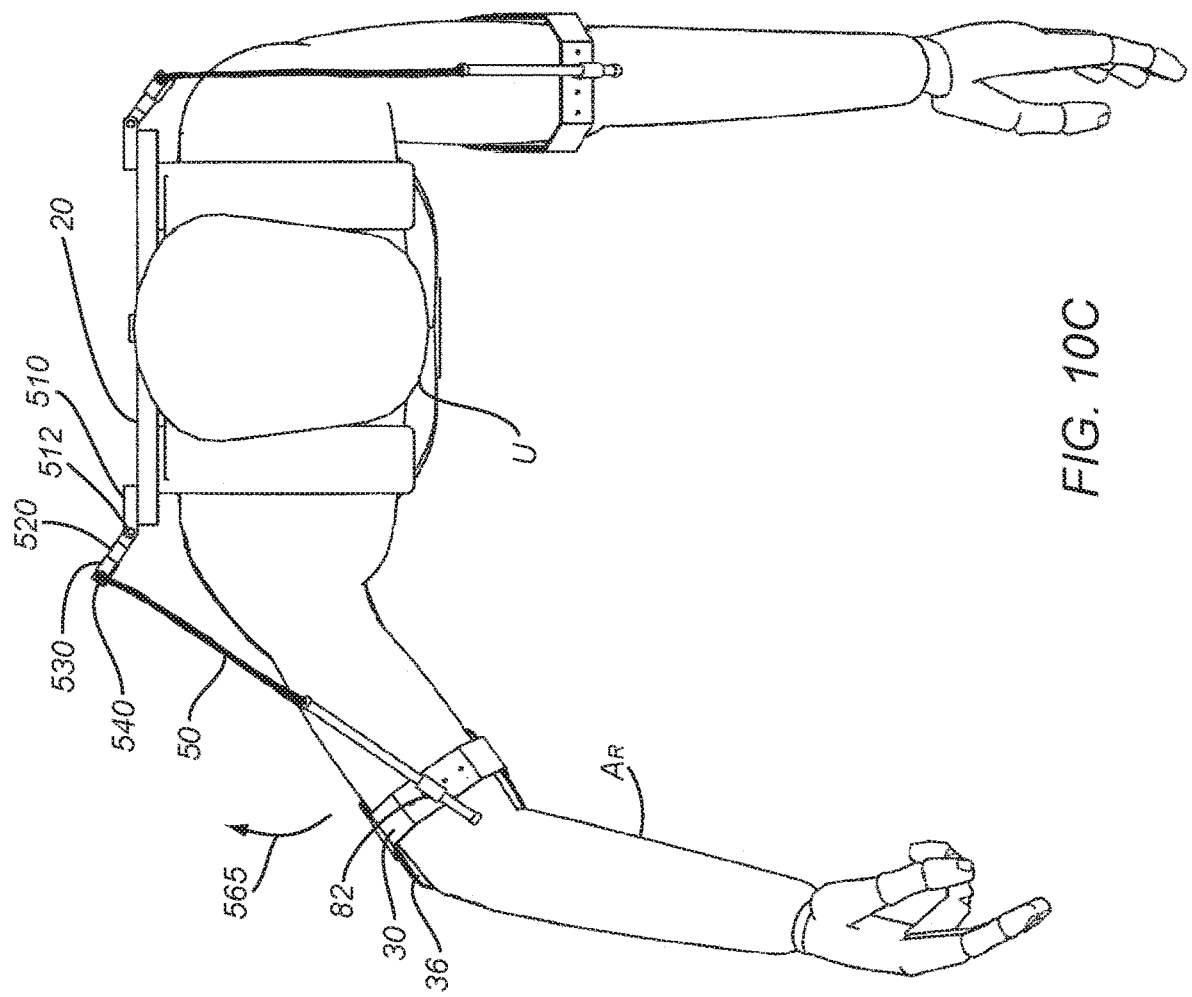

ADAPTIVE ARM SUPPORT SYSTEMS AND METHODS FOR USE

RELATED APPLICATION DATA

The present application is a continuation of application Ser. No. 13/563,728, filed Jul. 31, 2012, issuing as U.S. Pat. No. 9,999,534. The present application is also related to application Ser. No. 13/353,268, filed Jan. 18, 2012, which claims benefit of provisional applications Ser. Nos. 61/433, 840, filed Jan. 18, 2011, and 61/507,535, filed Jul. 13, 2011, the entire disclosures of which are expressly incorporated by reference herein.

FIELD OF THE INVENTION

The present invention relates to systems, devices, and methods for supporting a user's arms, for example, to adaptive arm support systems that support one or both of a user's arms, while allowing substantially free motion, e.g., to allow the user to perform one or more tasks for extended periods of time with one or both arms extended.

BACKGROUND

Numerous tasks require people to work with their arms outstretched. Examples include surgery, dentistry, painting, dishwashing, and product assembly. Persons engaged in such activities may experience fatigue from prolonged muscular efforts required to resist the force of gravity on their arms in order to keep them extended. Weak or disabled persons may experience fatigue performing daily tasks. Static arm rests on chairs and work tables are only effective if the task is performed within a relatively restricted area, for example, at a computer keyboard. Tasks that involve a greater range of motion are not aided by static armrests.

Thus, there is a need for an adaptive armrest or arm support system that may relieve fatigue experienced by persons performing tasks involving moderate to large ranges of motion.

SUMMARY

The present invention is directed to systems, devices, and methods for supporting a user's arms, for example, to adaptive arm support systems or devices that support one or both of a user's arms, while allowing substantially free motion, e.g., to allow the user to perform one or more tasks for extended periods of time with one or both arms extended.

In accordance with one embodiment, a system is provided for supporting an arm of a user that includes a harness configured to be worn by a user, e.g., on the user's torso; and an arm support coupled to the harness and configured to support a portion of an arm of the user, the arm support configured to accommodate movement of the arm while following the movement without substantially interfering with the movement. The arm support may be configured to at least partially offset a gravitational force acting on the arm as the user moves and the arm support follows the movement of the user's arm. For example, the arm support may transfer at least a portion of the weight of the user's arm to the torso or other region of the user's body and/or may apply an opposing force to at least partially offset the gravitational force acting on the arm.

In one embodiment, the system includes one or more compensation elements coupled to the arm support to at least partially offset a gravitational force acting on the arm as the user moves and the arm support follows the movement of the user's arm. For example, the compensation element(s) may include one or more compensation elements coupled to the arm support to at least partially offset the gravitational force acting on the arm of the user as the user moves without substantially interfering with movement of the user's arm.

In accordance with another embodiment, a system is provided for supporting an arm of a user that includes a harness configured to be worn by a user, e.g., on the user's torso, the harness defining a vertical axis extending generally parallel to a spine of the user wearing the harness. An arm support may be coupled to the harness and may include an arm rest configured to support a portion of an arm of the user, the support movable without substantially interfering in movement of the user's arm. The arm support may include one or more compensation elements coupled to the arm support to at least partially offset a gravitational force acting on the arm of the user as the user moves and the arm support follows the user's movement.

Optionally, a pair of arm supports and associated compensation elements may be coupled to the harness for supporting both arms of the user.

In one embodiment, the one or more compensation elements may include a resilient member including a first end coupled to the harness and a second end coupled to the arm supports. The resilient member may be biased to a predetermined orientation, e.g., a substantially straight configuration, yet may be resiliently deflectable to accommodate movement of the arm of the user and/or provide a lifting or other reactive force to at least partially offset a gravitational force acting on the arm during movement.

Optionally, a set of compensation elements may be provided and the user may select one or more compensation elements to couple between the harness and the arm support. For example, multiple compensation elements may be coupled between the harness and the arm support to increase the support provided. In addition or alternatively, individual compensation elements may be provided having different stiffness and/or flexibility characteristics such that a user may select one or more compensation elements having desired properties and couple them between the harness and the arm support.

In accordance with still another embodiment, a method is provided for supporting an arm of a user during one or more tasks. A harness may be placed on the user, the harness comprising an arm support movable relative to the harness and including an arm rest. A portion of the user's arm may be supported using the arm rest such that the arm support subsequently follows movement of the user's arm. The user may then perform one or more tasks involving movement of the user's arm, the arm support at least partially offsetting a gravitational force acting on the user's arm during the movement without substantially interfering in the movement.

In accordance with yet another embodiment, a method is provided for supporting an arm of a user during one or more tasks using a system including a harness, an arm support, and one or more, e.g., a plurality of compensation elements. One or more of the compensation elements may be selected and coupled between the harness and the arm support. The harness may be placed on the user and the arm support may be coupled to the user's arm. The user may then perform one or more tasks involving movement of the user's arm, the one or more compensation elements coupled between the harness and the arm support at least partially offsetting a gravitational force acting on the user's arm during the movement.

Thus, the devices, systems, and methods herein may counterbalance all or part of the weight of one or both of a user's arms as the user performs one or more tasks, which may reduce arm and/or shoulder muscle fatigue and/or improve the user's steadiness and precision. In addition or alternatively, the arm support systems herein may adaptively reposition with the user, e.g., following movement of the user's arms as the user performs normal tasks without substantially interfering with the tasks. For example, the weight of one or both of the user's arms may be transmitted into the harness via a system of arm rests and compensation elements. Thus, with the harness worn or otherwise attached to the user, the system may transmit at least a portion of the weight of the user's arm(s) to the user's abdomen, shoulder, hips, sides, or other regions of the user's torso, which may be more readily adapted to receive and resist such forces without undue muscle fatigue and/or discomfort.

Other aspects and features of the present invention will become apparent from consideration of the following description taken in conjunction with the accompanying drawings.

BRIEF DESCRIPTION OF THE DRAWINGS:

It will be appreciated that the exemplary apparatus shown in the drawings are not necessarily drawn to scale, with emphasis instead being placed on illustrating the various aspects and features of the illustrated embodiments.

FIGS. 6A and 6B are details of the attachment of compensation elements to a body-mountable adaptive arm support system.

FIG. 10C is a top view of the adaptive arm support system of FIGS. 10A and 10B.

DETAILED DESCRIPTION

Figure 1:
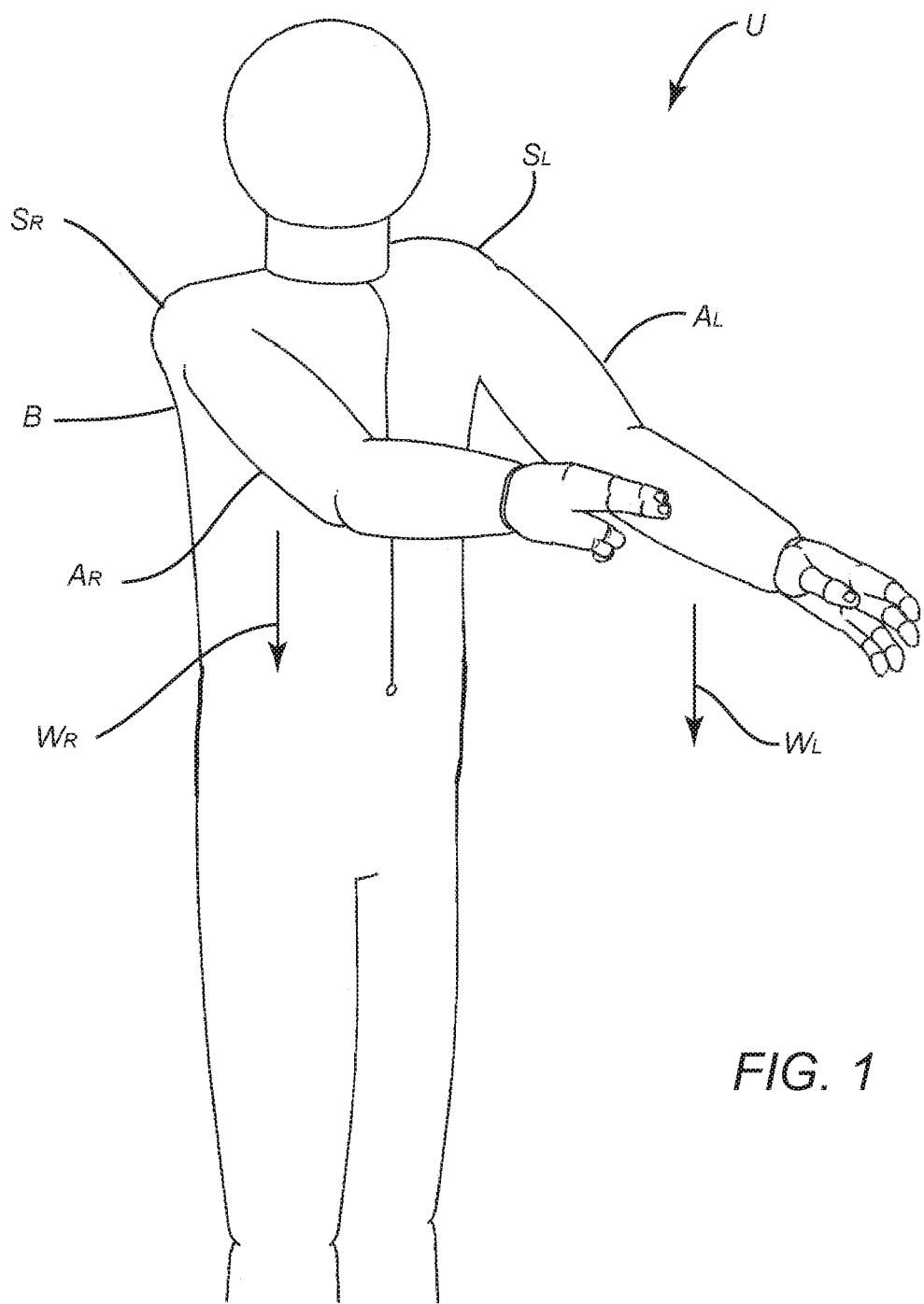
FIG. 1 is a perspective view of a person with arms outstretched.

Persons performing tasks with one or both of their arms outstretched for long periods of time may experience fatigue. As shown in FIG. 1, the force of gravity Wl and Wr on the outstretched arms 5 of a user U must be resisted by muscles in the user's shoulders Sr and Sl, and back B. Over long periods of time, this may result in fatigue, and a corresponding degradation in performance and accuracy. Surgeons, for example, may need to move and hold their arms partially or fully outstretched for long periods of time. Many report problems with fatigue, tremors, and reduced accuracy. In some cases, surgeons are unable to perform procedures daily, but instead have to rest for a day between operations. Static armrests, such as those commonly found on armchairs, provide arm support, but are effective only in a limited range of positions. Therefore, there is a need for an arm support system which supports the user's arms over a greater range of motions.

To address this need, the present application provides various adaptive arm support systems that support one or both of a user's arms, e.g., substantially vertically, while allowing substantially free motion of the arm(s), e.g., in multiple directions and elevations, to allow the user to perform one or more tasks for extended periods of time with the arm(s) extended.

As used herein, "vertical" generally means substantially vertical, i.e., along a vertical axis extending generally parallel to the spinal column of the user U. Thus, although the user U may generally stand substantially erect during activities while wearing the adaptive arm support systems herein, the user U may move in ways to skew the vertical axis off of true vertical. As used herein, "horizontal" generally means substantially horizontal, i.e., along a horizontal axis that extends orthogonally, e.g., substantially perpendicular, to the vertical axis extending generally parallel to the spinal column of the user U. For example, the horizontal axis may extend generally parallel to an axis extending between the shoulders of the user U.

Figure 2:
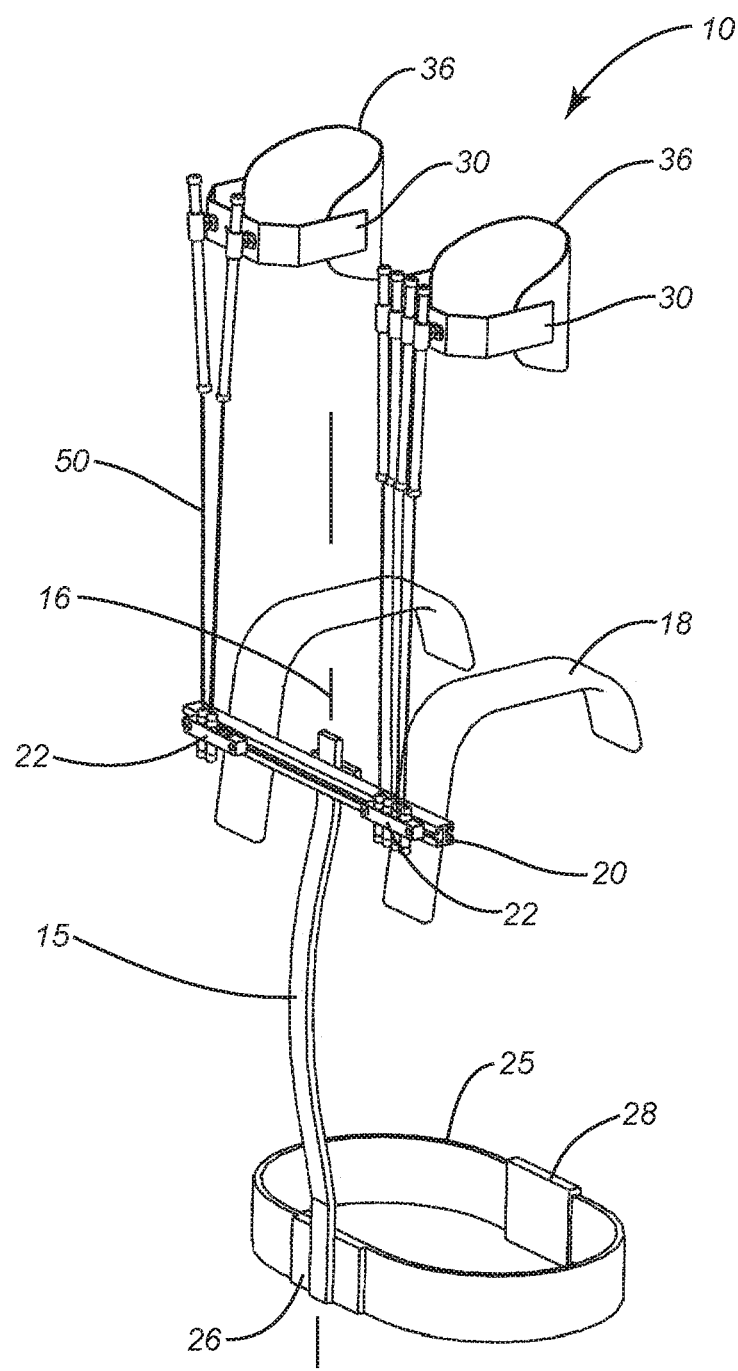
FIG. 2 shows a rear perspective view of an exemplary embodiment of a body-mountable adaptive arm support system configured to be worn by a user.

Turning to FIG. 2, a first exemplary embodiment of an adaptive arm support system 10 is shown. Shoulder brackets 18 are connected to cross bar 20, which joins vertical bar 15. Vertical bar 15 further connects to belt 25 at belt connection plate 26. Vertical bar 15 may be rigid, semi-rigid, or flexible, and may have a cross-section that is rectangular, square, round, oval, or any other shape or combinations thereof, and may pivot or flex relative to belt connection plate 26 (not shown). For example, the vertical bar 15 may be sufficiently flexible or malleable to allow the user U to bend over or otherwise move, while providing sufficient column strength and/or other support between the cross bar 20 and the belt 25. Shoulder brackets 18, cross bar 20, vertical bar 15, and belt 25 together form a structure, e.g., a harness, that may be connected to the abdomen of user U, and which may define a substantially vertical axis 16 aligned with the spine of the user U for the components carried by or otherwise coupled to the harness. Belt 25 may be rigid, semi-rigid, rigid in one plane, rigid in certain regions, or flexible. A belt closure 28 is provided to permit tightening of belt 25. Belt 25 may be secured around the user's waist, hips, or other region of the user's abdomen such that the vertical bar 15 (and vertical axis 16) is substantially aligned with the user's spine, and the cross bar 20 is mounted substantially horizontal in the region adjacent to the user's shoulders. Straps, belts, or other fastening devices (not shown) may be provided to further secure adaptive arm support 10 to user U, e.g., in addition to or instead of the components described herein, such as those disclosed in application Ser. No. 13/353,268, incorporated by reference herein.

As shown, the cross bar 20 provides mounting points for mounting blocks 22, which provide attachment points for one or more compensation element(s) 50. Compensation element(s) 50 are, in turn, attached to arm brackets 30. Arm rests 36 may be attached to arm brackets 30, e.g., to enhance supporting and/or coupling a user's arms to the compensation element(s) 50. These elements may be collectively formed into a harness, a jacket, a shirt, or other garment, and may be worn outside of, underneath, or instead of other clothing.

Figure 3A:
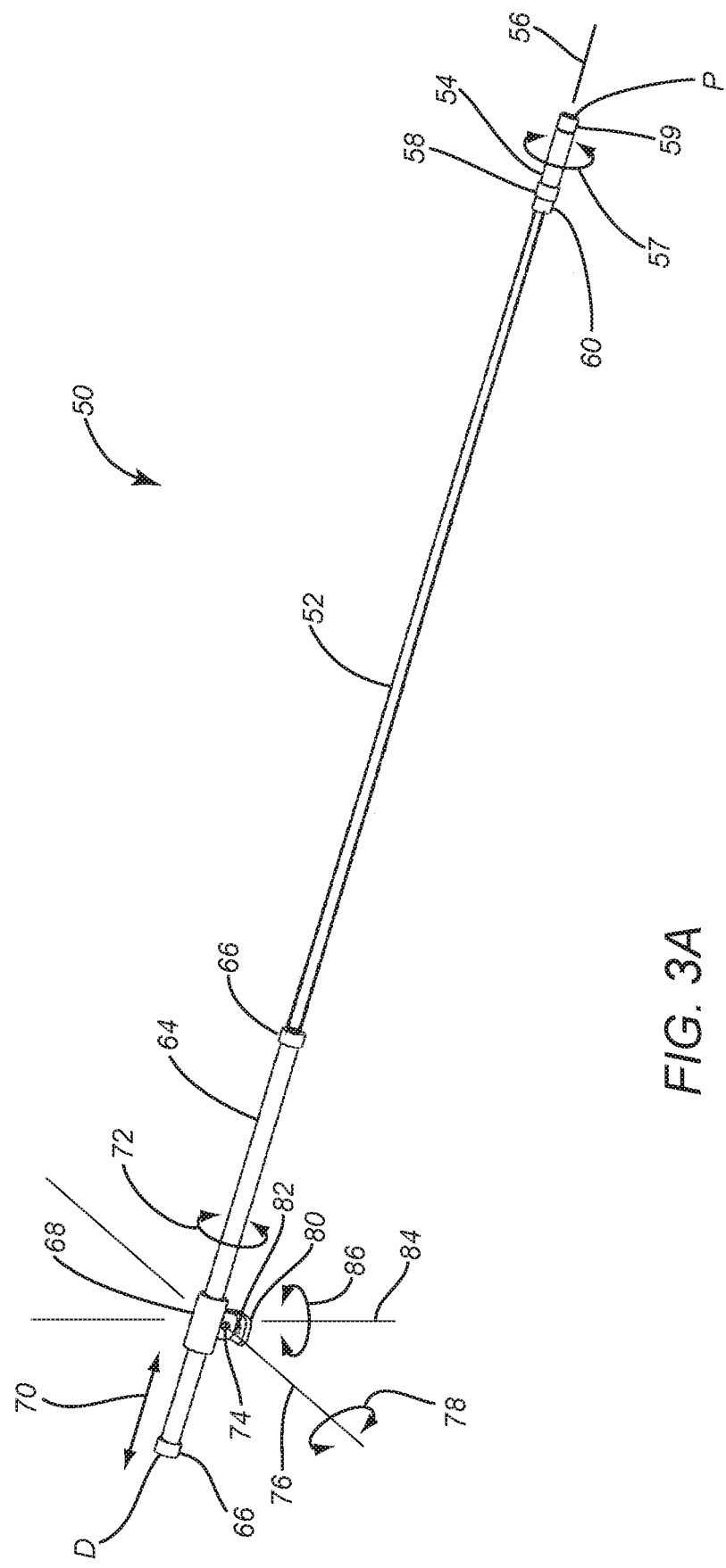
FIGS. 3A and 3B show perspective and exploded views, respectively, of an exemplary compensation element for a body-mountable adaptive arm support system.

Referring now to FIG. 3A, an exemplary compensation element 50 is shown that includes a proximal end P and a distal end D. As shown, an elongate resilient member 52, which may be composed of metal, polymer, composite, and/or other material (and which may formed as a solid, tubular, or other hollow member, e.g.,, woven, segmented, formed as a single rod or a bundle of rods, and the like) is attached at one end to a mounting pivot 54 at the proximal end P of the compensation element 50. In an exemplary embodiment, the resilient member 52 may have super-elastic properties, such as those associated with super-elastic Nitinol. Resilient member 52 may be substantially straight, or may be curved in its relaxed state, e.g., biased to a predetermined configuration when free from external sources. Mounting pivot 54, which encircles or is otherwise coupled to the resilient member 52, may optionally rotate relative to the resilient member 52, e.g., about rotate axis 56, as shown by rotate path 57. A stop collar 58 may be disposed on the mounting pivot 54 to aid in positioning, as described below. Locating collars 59 and 60, which may be rigidly attached to the resilient member 52, may maintain the position of the mounting pivot 54 along the resilient member 52.

Figure 3B:
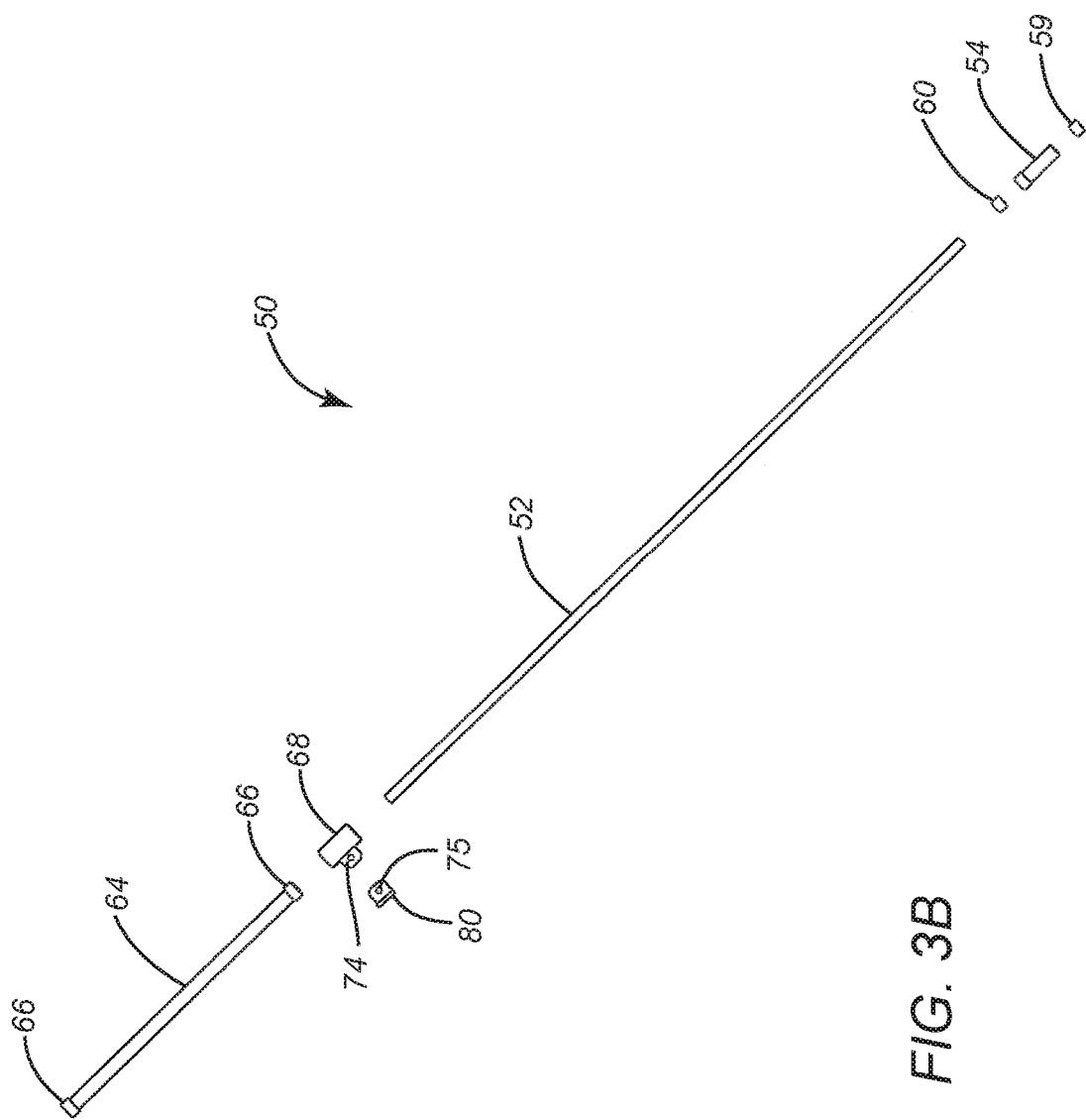

The resilient member 52 may also be rigidly attached at its other end to slide rod 64. The far end of the slide rod 64 may define the distal end D of the compensation element 50. The slide rod 64 is encircled by or otherwise coupled to slide mount 68, and may translate axially relative to slide mount 68 along slide path 70, and/or rotate relative to slide mount 68 along rotate path 72. Optionally, slide rod 64 may be fixed relative to slide mount 68, or may be fixed axially relative to slide mount 68 while remaining free to rotate relative to slide mount 68. As shown, the slide rod 64 includes one or two limit stops 66, which ensure that the slide rod 64 does not come out of the slide mount 68. The slide mount 68 also includes slide mount pivot 74, at which it is attached to slide mount anchor 80, and which defines pivot axis 76. The slide mount 68 may pivot relative to the slide mount anchor 80 about the pivot axis 76, along pivot path 78. The slide mount anchor 80 may also include anchor pivot 82, which defines pivot axis 84, about which the slide mount anchor 80 (and thus the slide mount 68) may pivot along pivot path 86. FIG. 3B is an exploded view of the compensation element 50. The slide mount pivot 74 in the slide mount 68 may form a rotatable connection with anchor slide pivot 75 in the slide mount anchor 80.

Figure 3C:
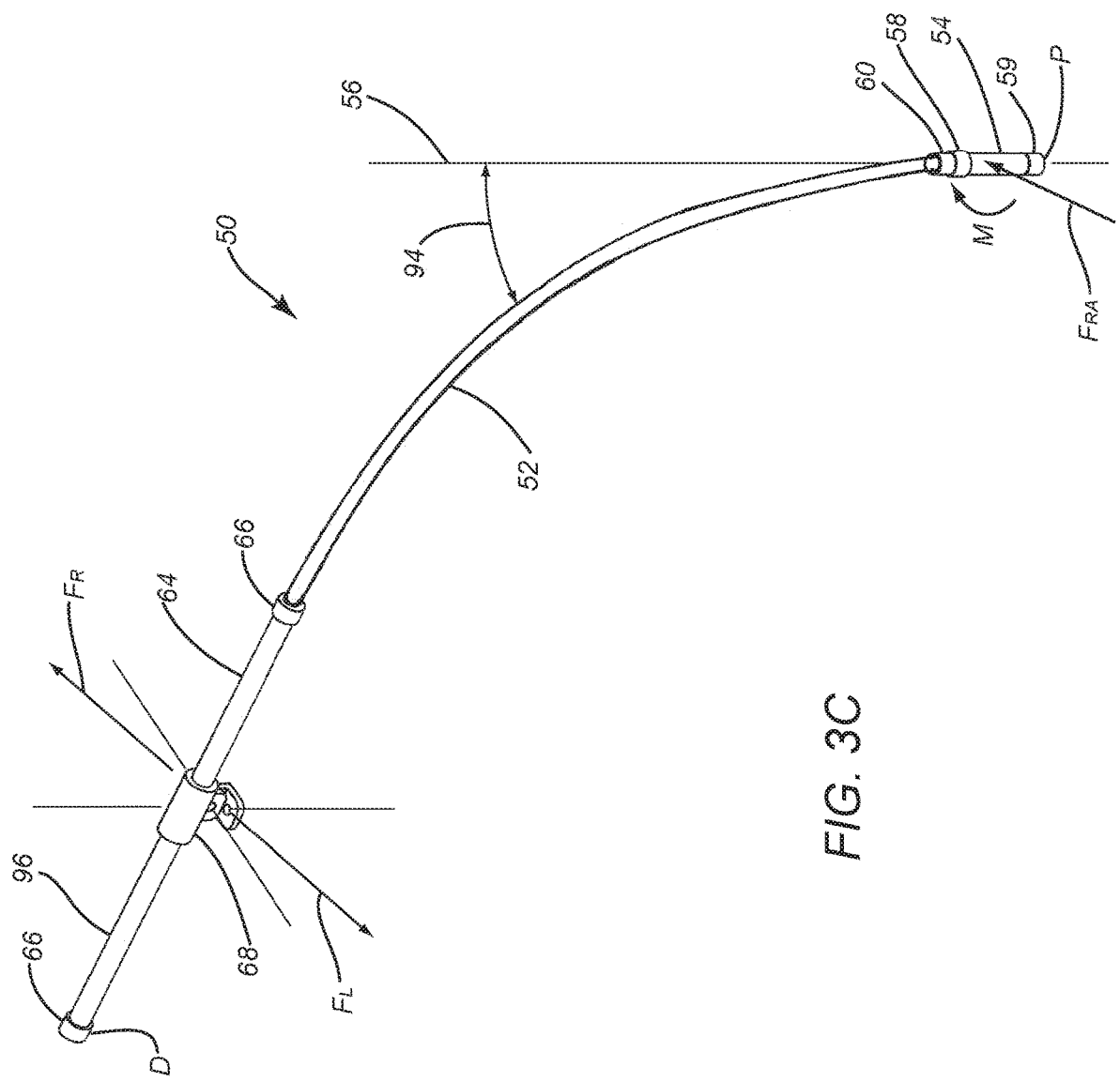
FIG. 3C is a perspective view of the compensation element of FIGS. 3A and 3B, subjected to an external force causing the compensation element to curve.

FIG. 3C shows the compensation element 50 deflected away from the rotate axis 56 in response to a load Fl, approximately along deflection path 94. The resilient member 52 is shown bending in response to load Fl, and in response to this deflection creates a restoring force Fr, acting opposite load Fl. The properties of the resilient member 52 may be modified to increase or decrease the restoring force Fr, for example, by modifying the stiffness of the material used to manufacture the resilient member 52 and/or by increasing or decreasing the diameter and/or length of the resilient member 52. The material properties of the resilient member 52 may be chosen to provide a more consistent restoring force Fr through a large range of deflections. For example Nitinol wire, used within accepted parameters of strain, may provide more consistency in restoring force Fr. Alternatively, the properties of the resilient member 52 may be chosen to provide a progressively greater or otherwise variable restoring force Fr during its desired range of deflections. A reaction moment M and reaction force Fra at the proximal end P counteracts load Fl, and acts to maintain substantial static balance. As shown, the slide rod 64, generally more rigid than the resilient member 52, may remain substantially straight during such movement.

Figure 4A:
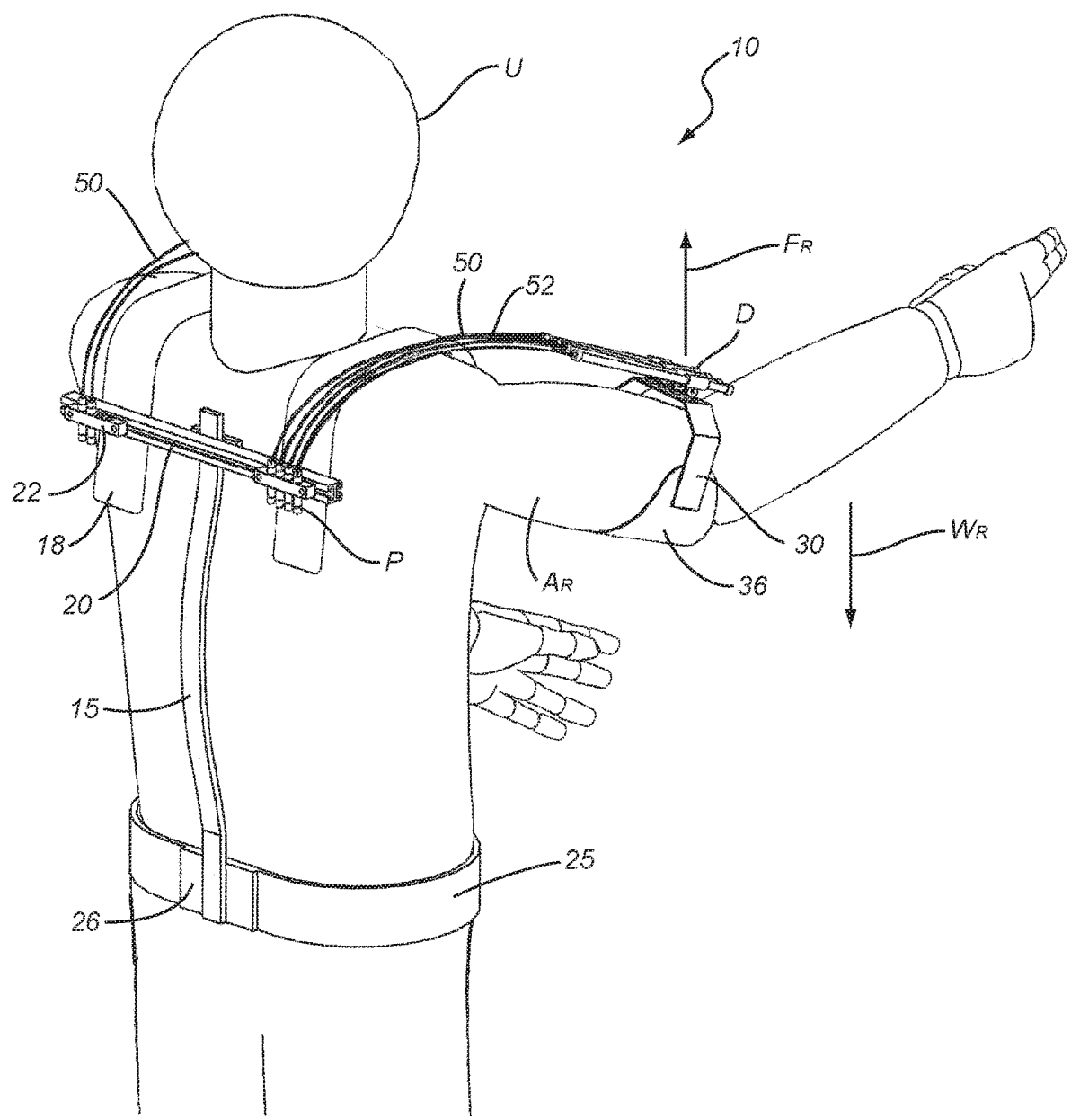
FIGS. 4A-4C are perspective views of an exemplary body-mountable adaptive arm support system being worn by a user with different arm positions of the user.
Figure 4B:
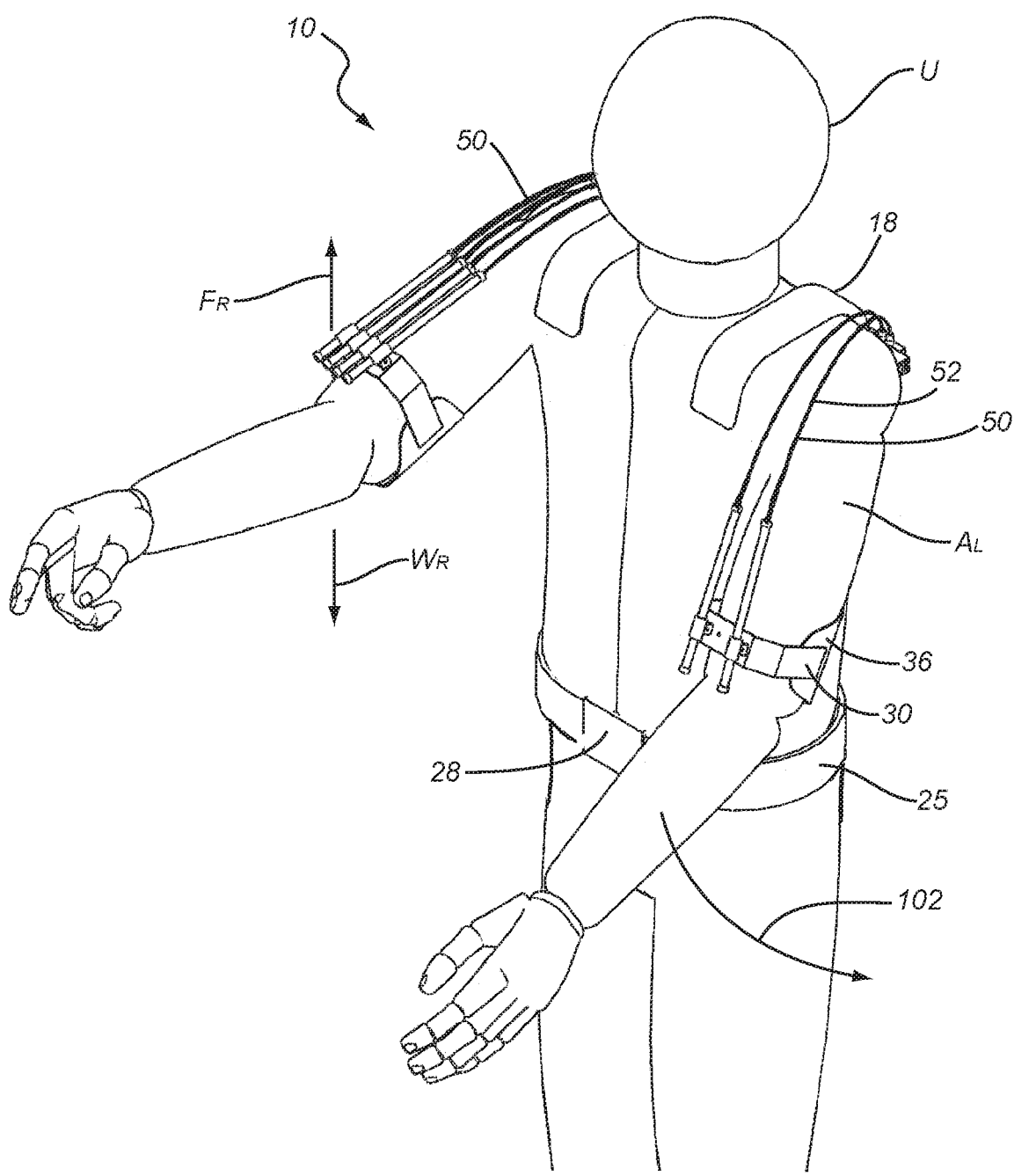
Figure 4C:
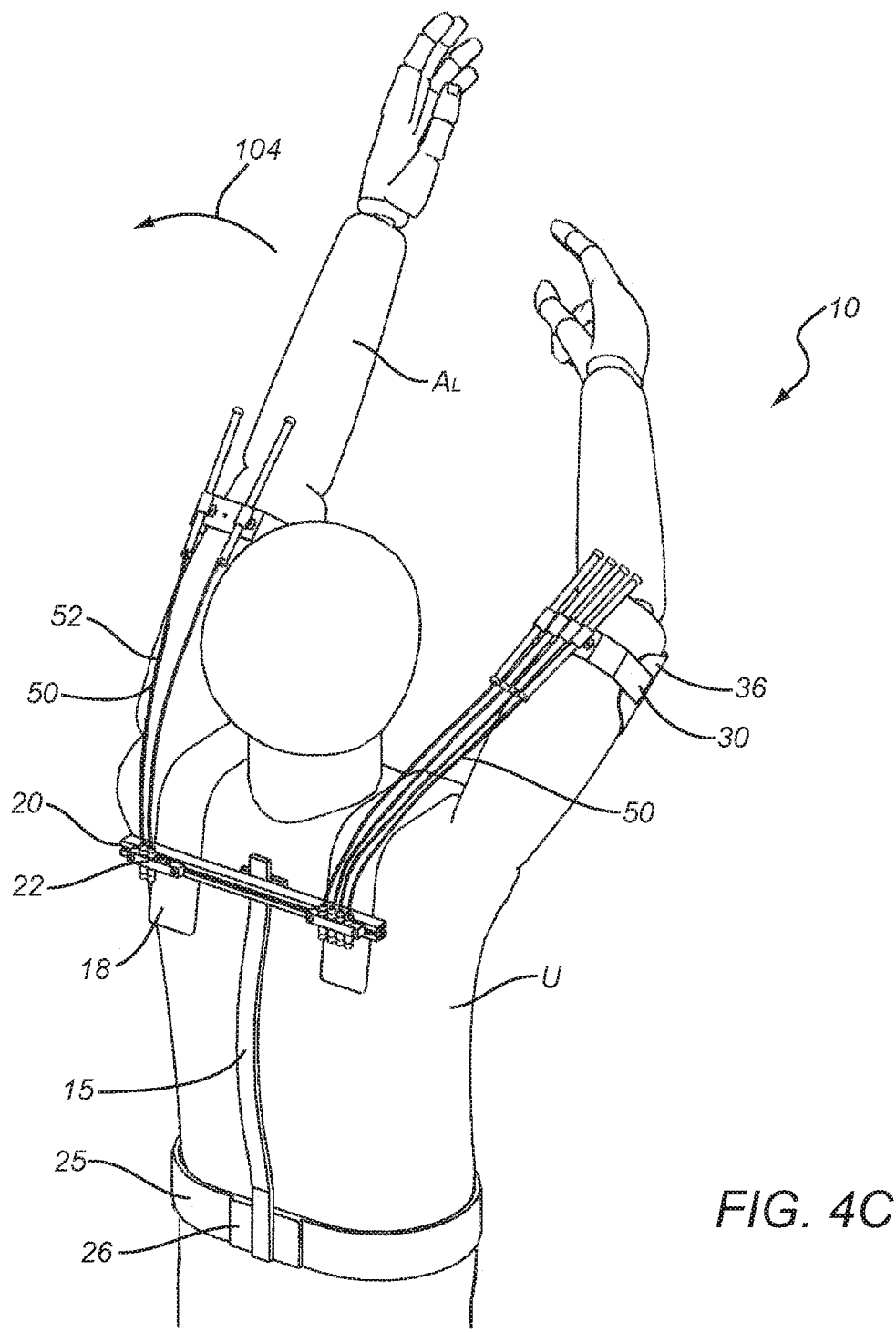

Referring now to FIG. 4A-FIG. 4C, adaptive arm support 10 is shown worn by or otherwise attached to user U. FIG. 4A, a semi-perspective view from behind, shows the user U's right arm Ar inserted into adaptive arm support 10. Arm rest 36 is positioned on the underside of arm Ar. Arm bracket 30, attached to the arm rest 36, connects the arm rest 36 to the distal end D of one or more compensation element(s) 50 (as described in greater detail below). FIG. 4A shows, by way of example, four compensation elements 50 in use on the user U's right arm Ar. The resilient members 52 of compensation elements 50 are shown deflected by the weight of the user's arms, as shown in FIG. 3C. The proximal ends P of the compensation elements 50 connect to mounting blocks 22, which in turn attach to cross bar 20, and the resilient members 52 pass over the user's shoulder from the cross bar 20 to the arm bracket 30 without contacting the shoulder when the harness and arm rest 36 are worn by the user U. Restoring or lifting force Fr, created by deflected compensation elements 50 (defined in FIG. 3C), acts in response to the weight Wr of the user U's right arm Ar, acting to lift or counterbalance all, or a portion of, the weight Wr and reduce the muscular effort the user U needs to employ to hold the arm Ar outstretched. FIG. 4B, a semi-perspective view of the front of the user U, shows the user U's left arm Al (in this case supported by only two compensation elements 50) lowered approximately along path 102, demonstrating the ability of the adaptive arm support 10 to react to movements of the user U's arms. In this case, the resilient members 52 have deflected further than shown in FIG. 4A. Similarly, FIG. 4C shows the user U's left arm Al lifted upward approximately along path 104, in which case the resilient elements 52 are deflected less than shown in FIG. 4A. Thus, the adaptive arm support 10 is able to accommodate infinite positions of the user U's arms, and the user U may be able to move their arms to desired positions, while the adaptive arm support system 10 moves with (or "adapts to") the user U's arms, simultaneously supporting them without substantially interfering with the movement.

As shown by FIGS. 4A-4C, the number of compensation elements may be varied as desired. This permits the user U to adjust the amount of compensation force in response to the weight of the user's arms, or the requirements of the task. If more force is desired, for example, if the user U's arms are heavy or the user U is expecting to hold heavy objects, more compensation elements 50 may be added, and conversely, if less force is desired, compensation elements 50 may be removed. For example, the user U may desire a light counterbalancing force that compensates for approximately 40% of the gravitational forces Wr and Wl that may act on the user's arms (under-compensation). In another example, the user U may desire a high counterbalancing force that compensates for approximately 115% of the gravitational forces Wr and Wl on the user's arms (over-compensation).

It is anticipated that in general a minimum of one compensation element 50 will be used, although the lifting or reaction force provided by an individual compensation element 50 may be varied, as described elsewhere herein.

Figure 5:
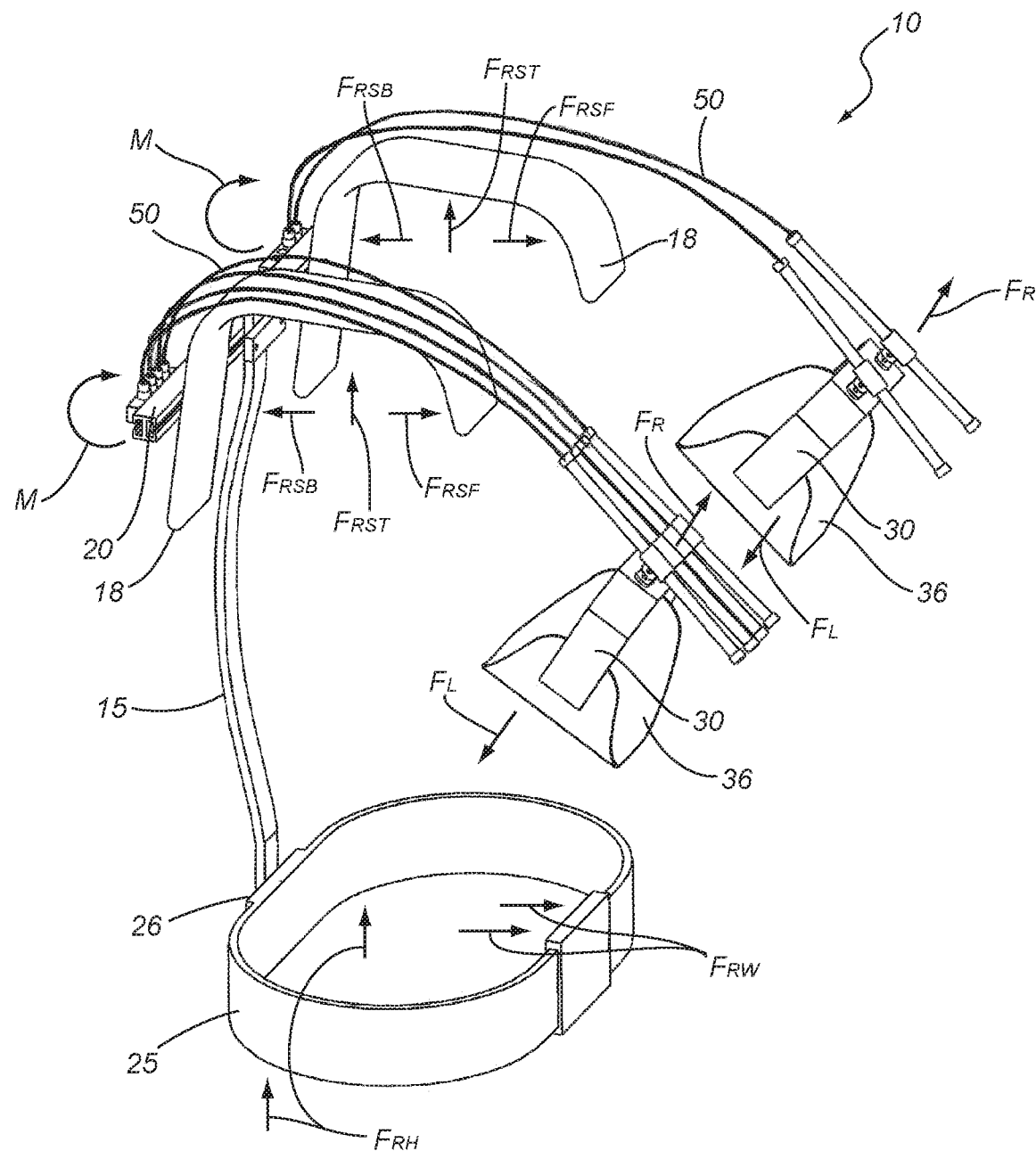
FIG. 5 shows reaction forces relevant to a body-mountable adaptive arm support system when the compensation elements are curved to accommodate movement of a user's arms.

FIG. 5 shows examples of reaction forces from the user's abdomen on an adaptive arm support 10, such as that shown in FIGS. 4A-4C. Shoulder brackets 18 and belt 25 make contact with the torso of the user U, at or around the abdomen, and provide surfaces for resisting the forces and/or torques input to the adaptive arm support system 10 by the user's arms Ar and Al to other portions of the user's body. Thus, other portions of the body may substantially bear the load of the user's arms, transmitted via the adaptive arm support 10, rather than the muscles of the user's back, shoulders, and/or arms themselves. For example, it may desirable that the areas of the abdomen bearing these loads do not require muscular activity to do so. Reaction force Frsb, for example, may be applied to the adaptive arm support 10 by a force from a portion of the user's back or shoulder. Frst and Frsf may be provided by the top and front of the user's shoulders. Similarly, Frw and Frh may result from contact with the user's waist and hips, respectively. These substantially static reaction forces require little work to maintain, and thus do not contribute significantly to the fatigue of the user U.

Figure 6A:
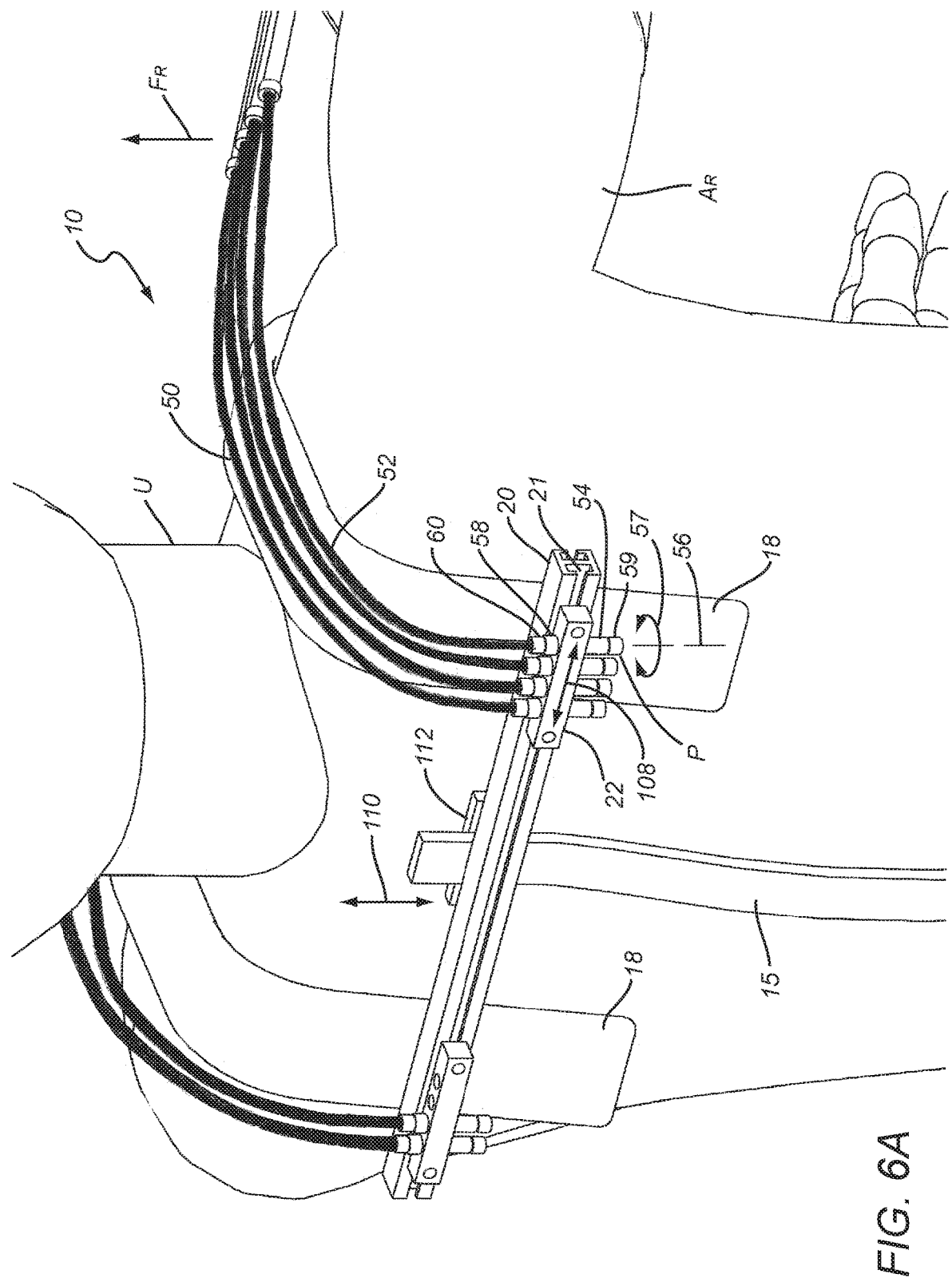

FIG. 6A shows a detail view of the attachment of the proximal end P of the compensation elements 50 to the harness, e.g., similar to that shown in FIG. 4A. As shown, the mounting pivot 54 of each compensation element 50, is seated into a recess (not shown) in the mounting block 22. The stop collar 58 locates the mounting pivot 54 relative to the mounting block 22. The resilient member 52 is able to rotate within the mounting pivot 54, about rotate axis 56 (as shown by rotate path 57). Thus, the compensation element(s) 50 are able to rotate about axis 56 in response to movement of the user U's arms in the course of performing a task. The mounting block 22 may accommodate one or more compensation elements 50, as desired. The mounting block 22 may provide arrangements of mounting pivots that differ from the linear pattern shown in FIG. 6A, for example square, or circular.

Optionally, the mounting block 22 may be repositioned along the cross bar 20 as desired by user U, for example, along path 108, using one or more releasable connectors (not shown), to accommodate the breadth of the user U's shoulders. In addition or alternatively, the cross bar 22 may be adjustable relative to the vertical bar 15, for example, along path 110, to accommodate the length of the user U's abdomen. Thus, the harness of the adaptive arm support 10 may be adjustable to accommodate the size and/or dimensions of the user U.

FIG. 6B is a detail view of attachment of the distal end D of the compensation element(s) 50 to the arm bracket 30, e.g., similar to that shown in FIG. 4A. The resilient members 52 may be rigidly attached to the slide rod 64, as shown in FIG. 3A. The slide rod 64 may translate relative to the slide mount 68, approximately along slide path 70, and/or rotate relative to the slide mount 68 along rotate path 72, e.g., to accommodate changes if the position of the arm bracket 30 resulting from motion of the user's arm Ar. The slide mount 68 may pivot relative to the slide mount anchor 80 about pivot axis 76 and/or along pivot path 78.

The slide mount anchor 80 may also include anchor pivot 82, which defines pivot axis 84, about which the slide mount anchor 80 (and thus the slide mount 68) may pivot along pivot path 86. The slide mount anchor 80 may be attached to the arm bracket 30 via a rotatable connection 115 at anchor pivot 82, for example, using a rivet or other rotatable fastener (not shown), permitting the slide mount anchor 80 (and thus the distal end D of the compensation element 50) to pivot approximately along pivot path 86. Restoring force Fr (described above in reference to FIG. 3C), acting through the rotatable connection 115, may be applied to the arm Ar via the arm bracket 30 and/or arm rest 36 and thus may oppose all or a portion of the force of gravity Wr. Thus, the compensation element(s) 50 (and the adaptive arm support system 10 in general) may provide a counterbalancing force while accommodating any motion and infinite position of the user's arm(s) as it "adapts to" the motion of the user U's arms, e.g., simultaneously supporting them without substantially interfering with the movement.

Figure 7A:
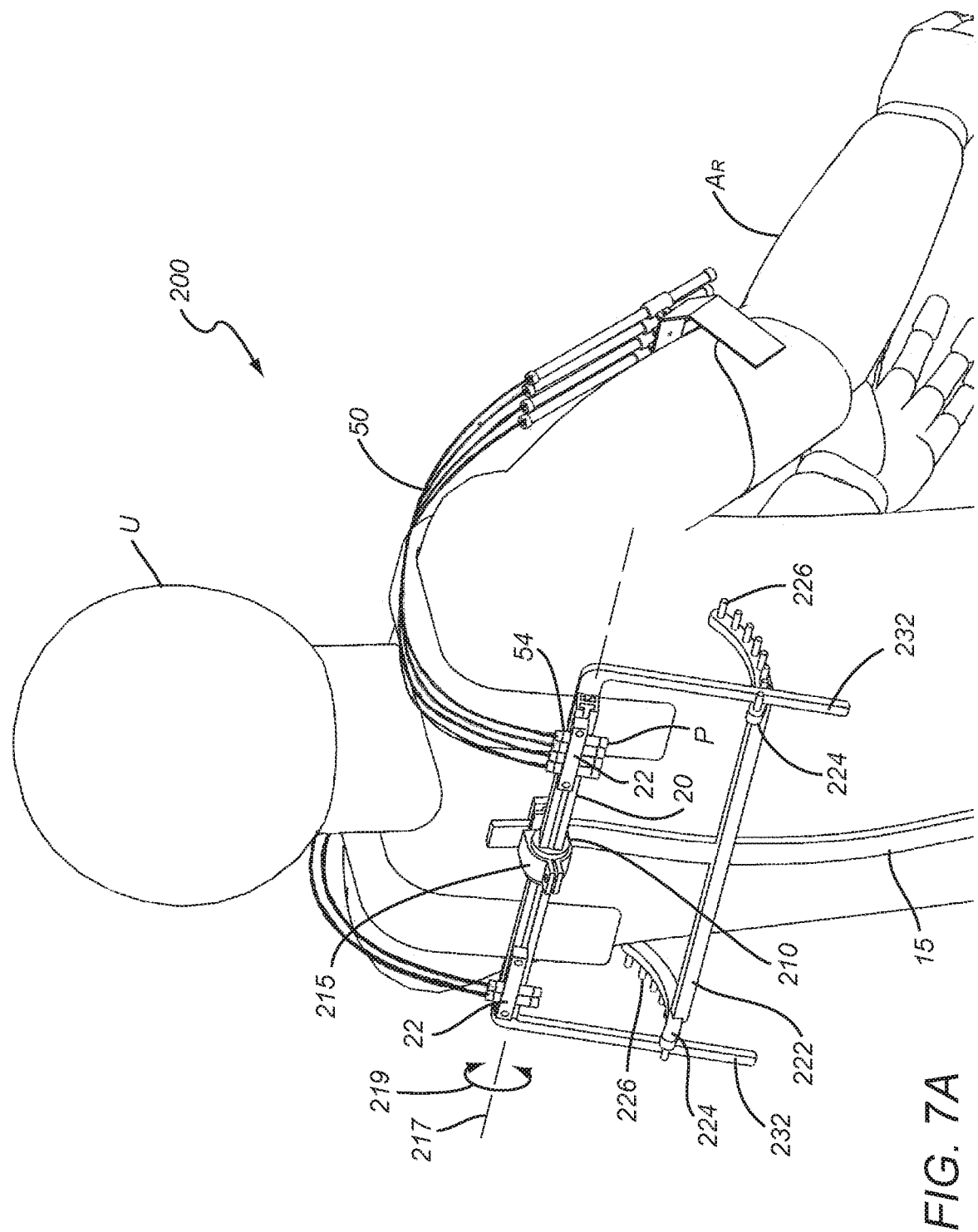
FIGS. 7A-7C are perspective and side views of an adjustable body-mountable adaptive arm support system.

FIG. 7A, a semi-perspective view from behind, shows another exemplary embodiment of an adaptive arm support system 200 with a position adjustment feature. Cross bar 20 is attached to cross bar hub 210. The cross bar hub 210, housed within cross bar rotate housing 215, and of generally circular cross section, is able to rotate relative to the cross bar rotate housing 215 about rotate axis 217, approximately along path 219. Mounting block 22, in which one or more mounting pivots 54 (at proximal end P of compensation element(s) 50) are seated, is attached to the cross bar 20, and thus may rotate along with the cross bar 20 about axis 219 (e.g., as described below).

Also, FIG. 7A shows features directed towards fixing the angular position of the cross bar 20 (e.g., once the cross bar 20 has been rotated relative to the cross bar rotate housing 215). Lock bar 222 is rigidly attached to vertical bar 15. Attached to the ends of the lock bar 222 are lock plates 224, which provide mounting for one or more lock features 226. Angle lock handle 232 is connected to the cross bar 20 and is configured to be positionable adjacent to one or more lock features 226, thereby fixing the angular position of the cross bar 20. The angle lock handle 232 may be attached to the cross bar 20 by rigid, flexible, or pivoting connection (not shown) in order to ease repositioning of the angle lock handle 232 adjacent to the appropriate lock features 226.

Figure 7B:
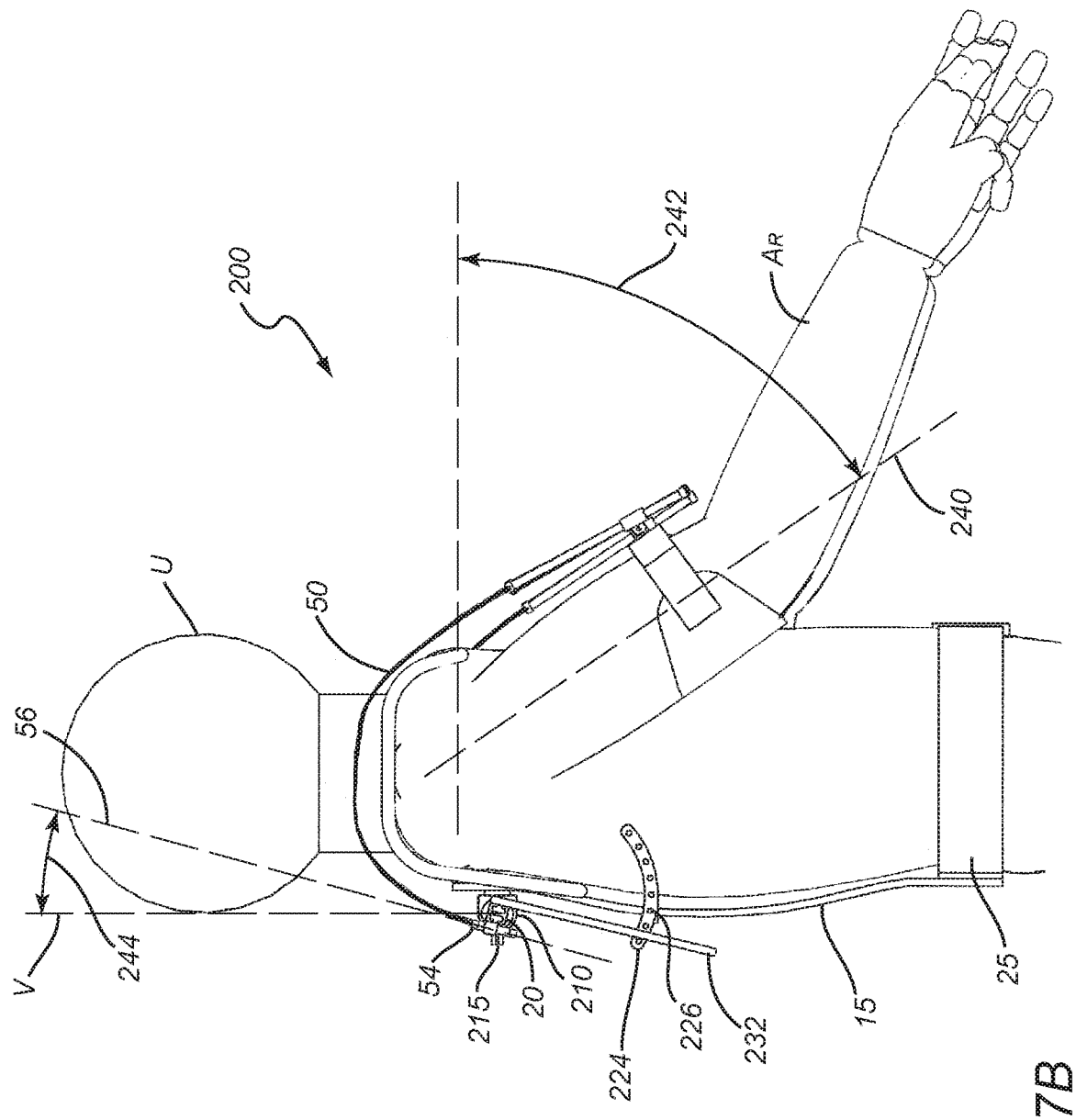

FIG. 7B is a side view of the adaptive arm support system 200, adjusted to favor lower positions of arm Ar (for example, in tasks that occur near waist level). The angle lock handle 232 is shown cooperating with the lock features 226 to tilt axis 56 of the mounting pivot(s) 54 forward relative to substantially vertical axis V, approximately by angle 244. The user's arm Ar is oriented approximately along axis 240, diverging from substantially horizontal axis H approximately by angle 242. In this position, the weight of the arm Ar may be 100% compensated for, i.e., at a neutral position. The user U may move the arm Ar freely in any direction, but little or no muscular effort may be required to maintain the position along axis 240.

Figure 7C:
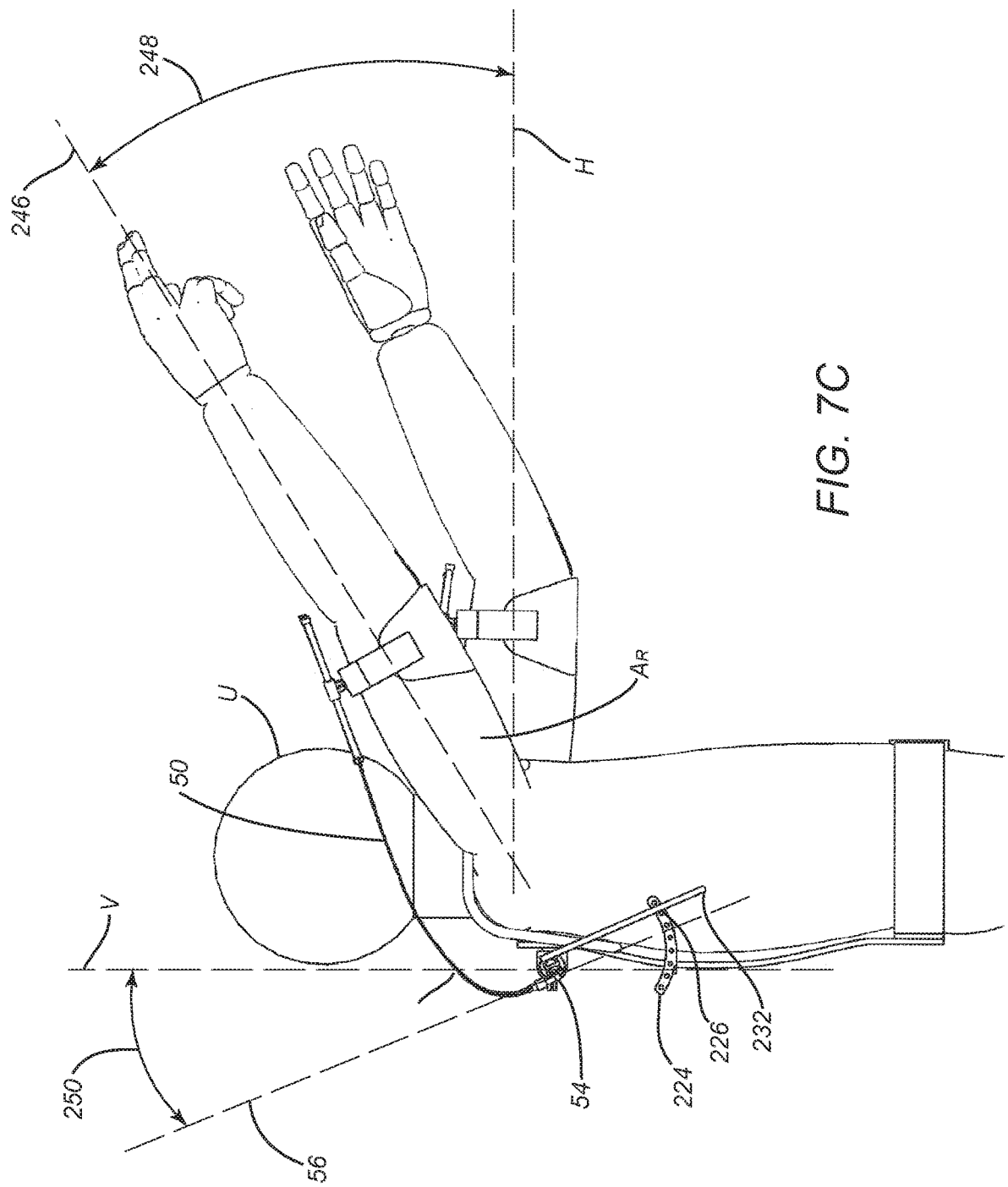

FIG. 7C is a side view of the adaptive arm support system 200, adjusted to favor higher positions of the arm Ar (for example, in tasks that occur overhead). The angle lock handle 232 is shown cooperating with the lock features 226 to tilt axis 56 of the mounting pivots 54 backward relative to substantially vertical axis V, approximately by angle 250. The user's arm Ar is oriented approximately along axis 246, diverging from substantially horizontal axis H approximately by angle 248. In this position, the weight of the arm Ar may be 100% compensated for, i.e., at a neutral position.

The user U may move the arm Ar freely in any direction, but little or no muscular effort may be required to maintain the position along axis 246. Thus, the adaptive arm support system 200 may be adjusted to provide a neutral position where desired, e.g., at a plurality of positions between a lower neutral position and an upper neutral position.

Figure 8A:
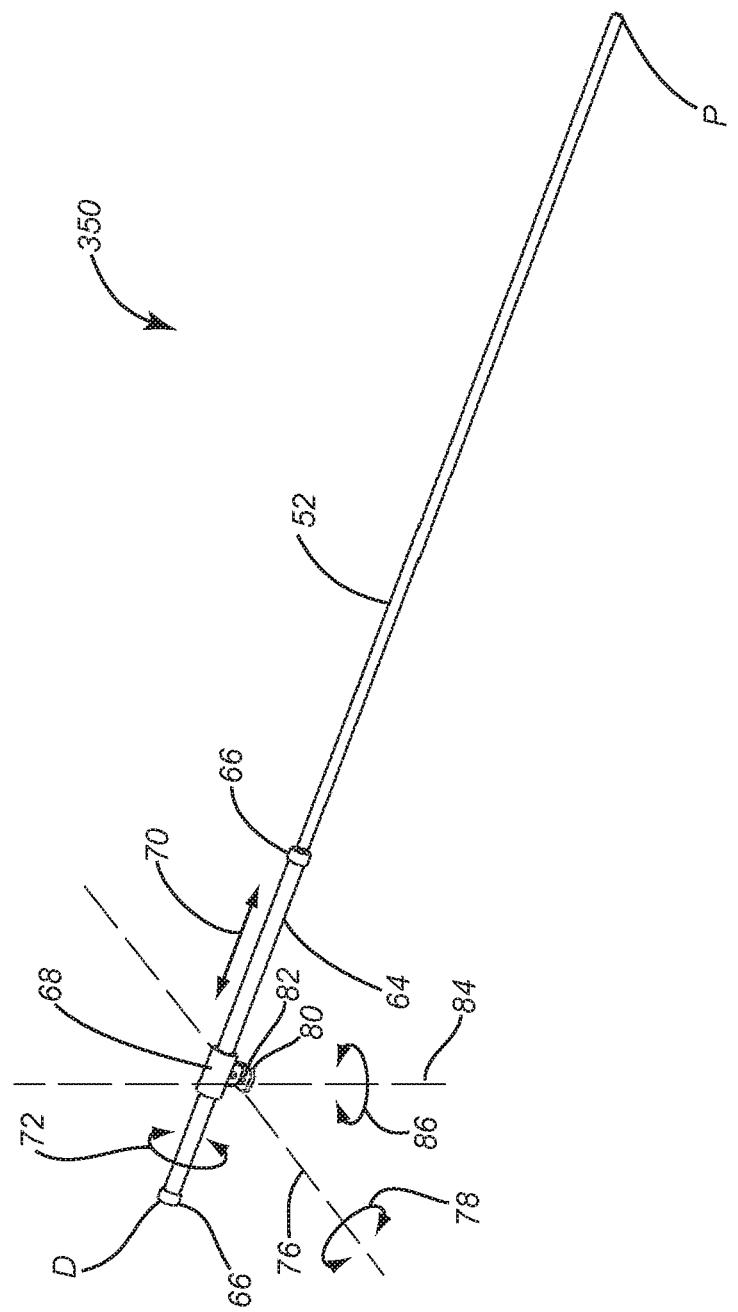
FIGS. 8A and 8B are perspective and detail views of a body-mountable adaptive arm support system with compensation elements joined at a single pivot.

FIG. 8A shows another embodiment of a compensation element 350, which differs from the previously described compensation elements by the absence of a mounting pivot at the proximal end P. Resilient member 52 is rigidly attached to one end of slide rod 64. The far end of the slide rod 64 defines distal end D. The slide rod 64 is encircled by slide mount 68, and may translate relative to the slide mount 68 along slide path 70, and/or may rotate relative to the slide mount 68 along rotate path 72. The slide rod 64 includes two limit stops 66, which may ensure that the slide rod 64 does not come out of the slide mount 68. The slide mount 68 also includes slide mount pivot 74, at which it is attached to slide mount anchor 80, and which defines pivot axis 76. The slide mount 68 may pivot relative to the slide mount anchor 80 about pivot axis 76 and/or along pivot path 78. The slide mount anchor 80 also includes anchor pivot 82, which defines pivot axis 84, about which the slide mount anchor 80 (and thus the slide mount 68) may pivot along pivot path 86.

Figure 8B:
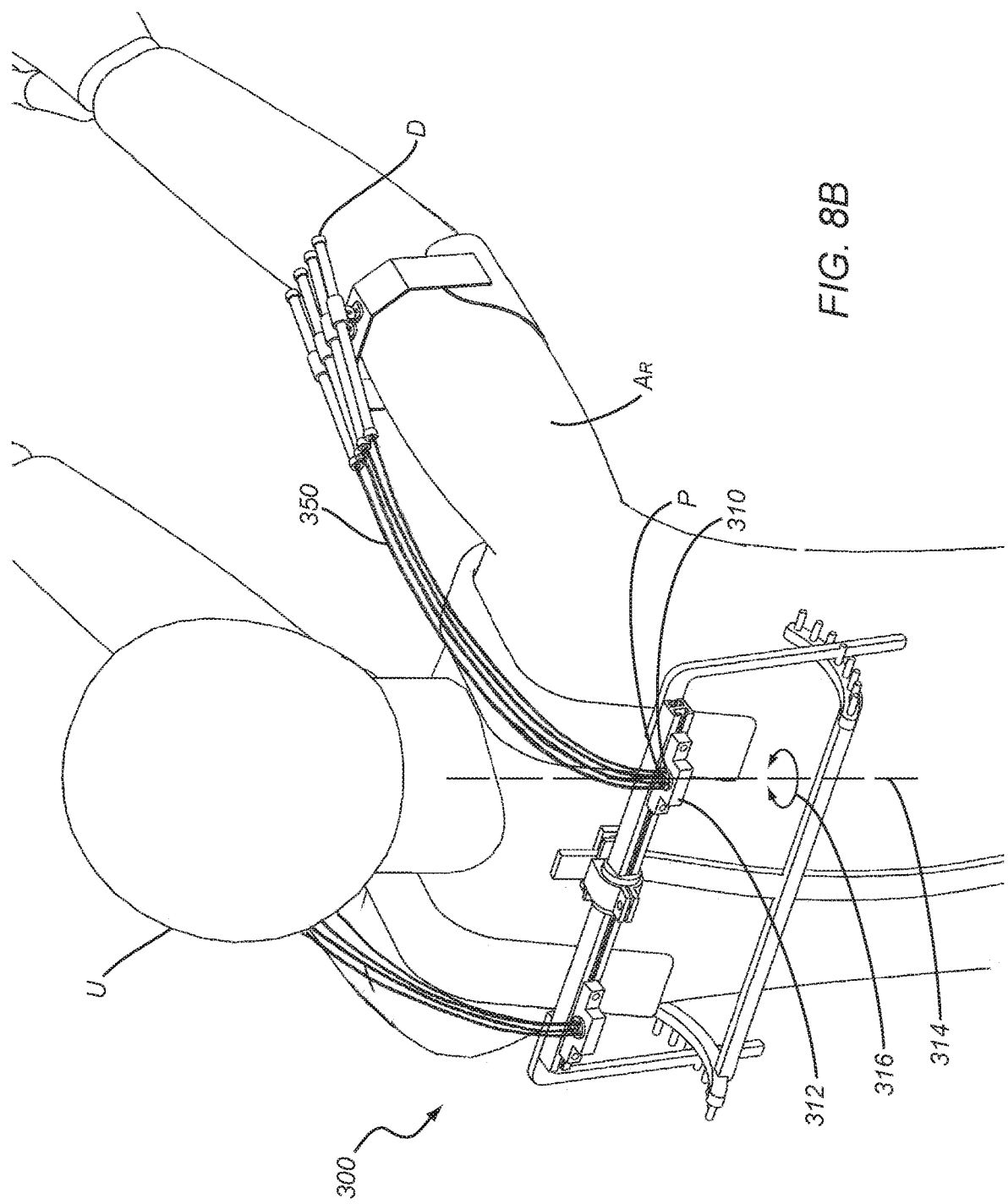

FIG. 8B shows an exemplary embodiment of an adaptive arm support system 300 including a single pivot mount for compensation elements 350. Proximal end(s) P of the compensation element(s) 350 may be rigidly attached to single pivot hub 310. The single pivot hub 310 is rotationally mounted to single pivot housing 312, and is free to pivot about pivot axis 314, approximately along path 316. Thus, one or more compensation elements 350 may pivot about a single axis 314 in response to the motion of user U's arm Ar, while providing a compensation force for the weight of the arm Ar.

Figure 9A:
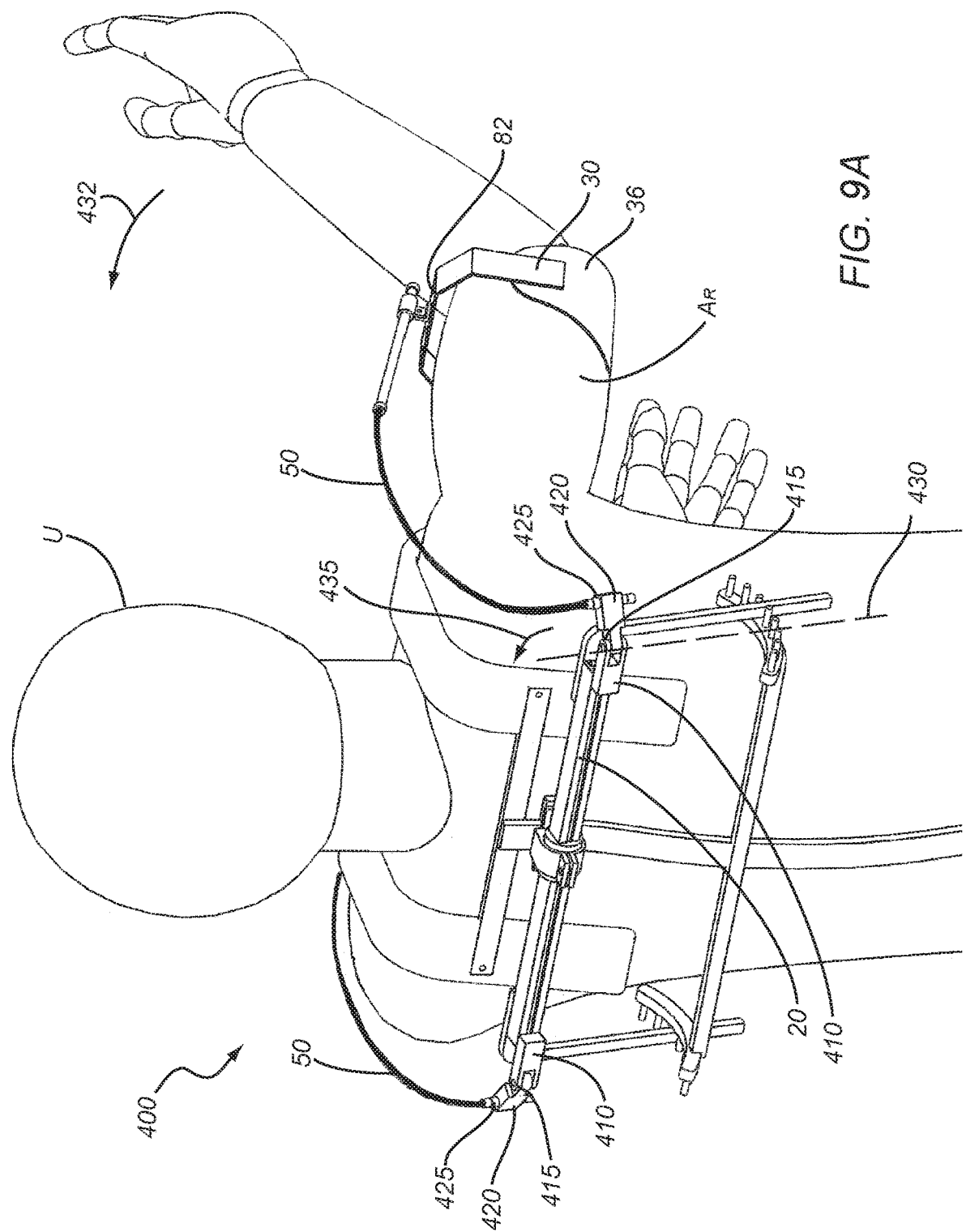
FIGS. 9A and 9B are perspective views of another exemplary embodiment of a body-mountable adaptive arm support system worn by a user, showing the user's right arm in different positions.
Figure 9B:
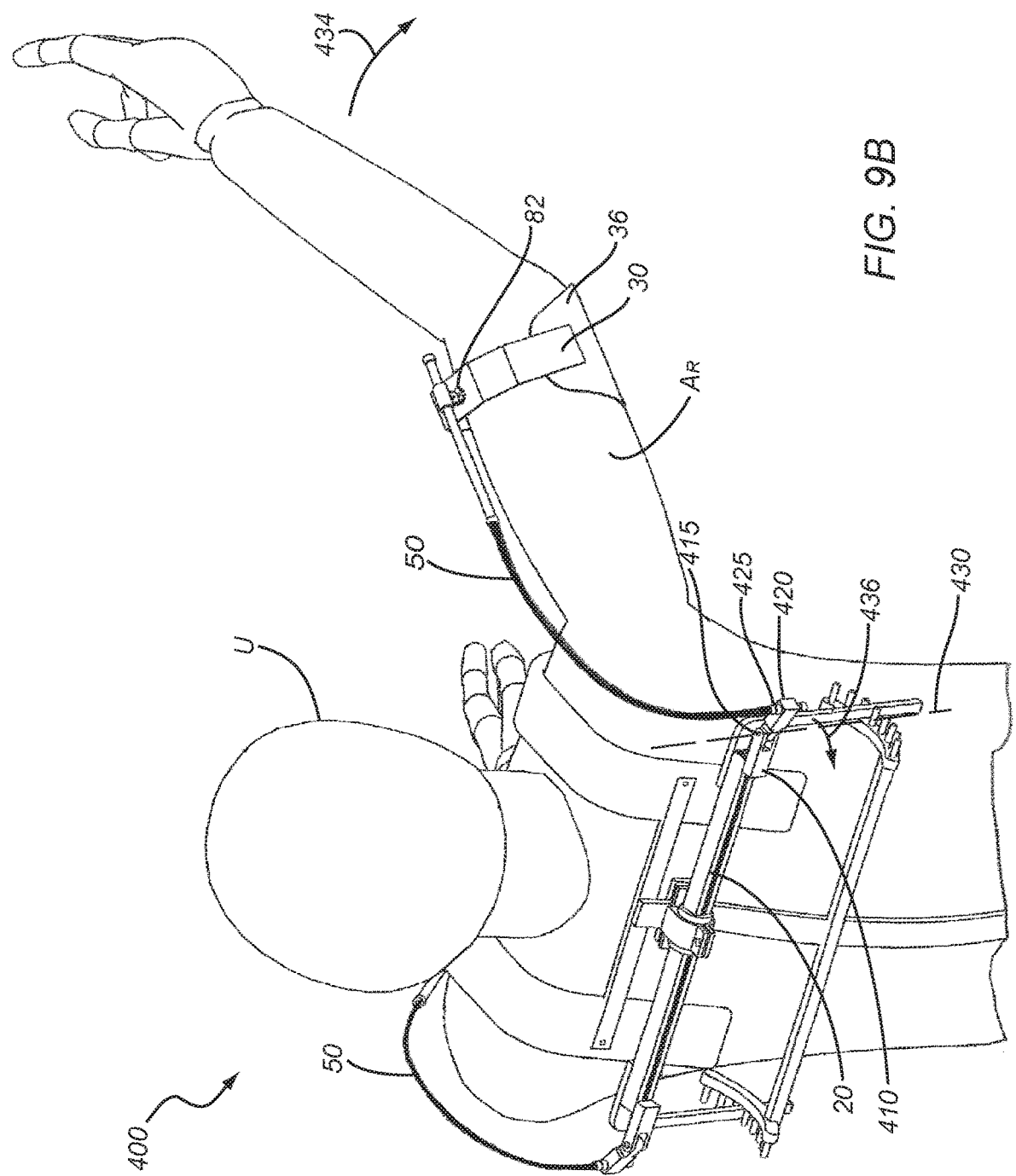
Figure 9C:
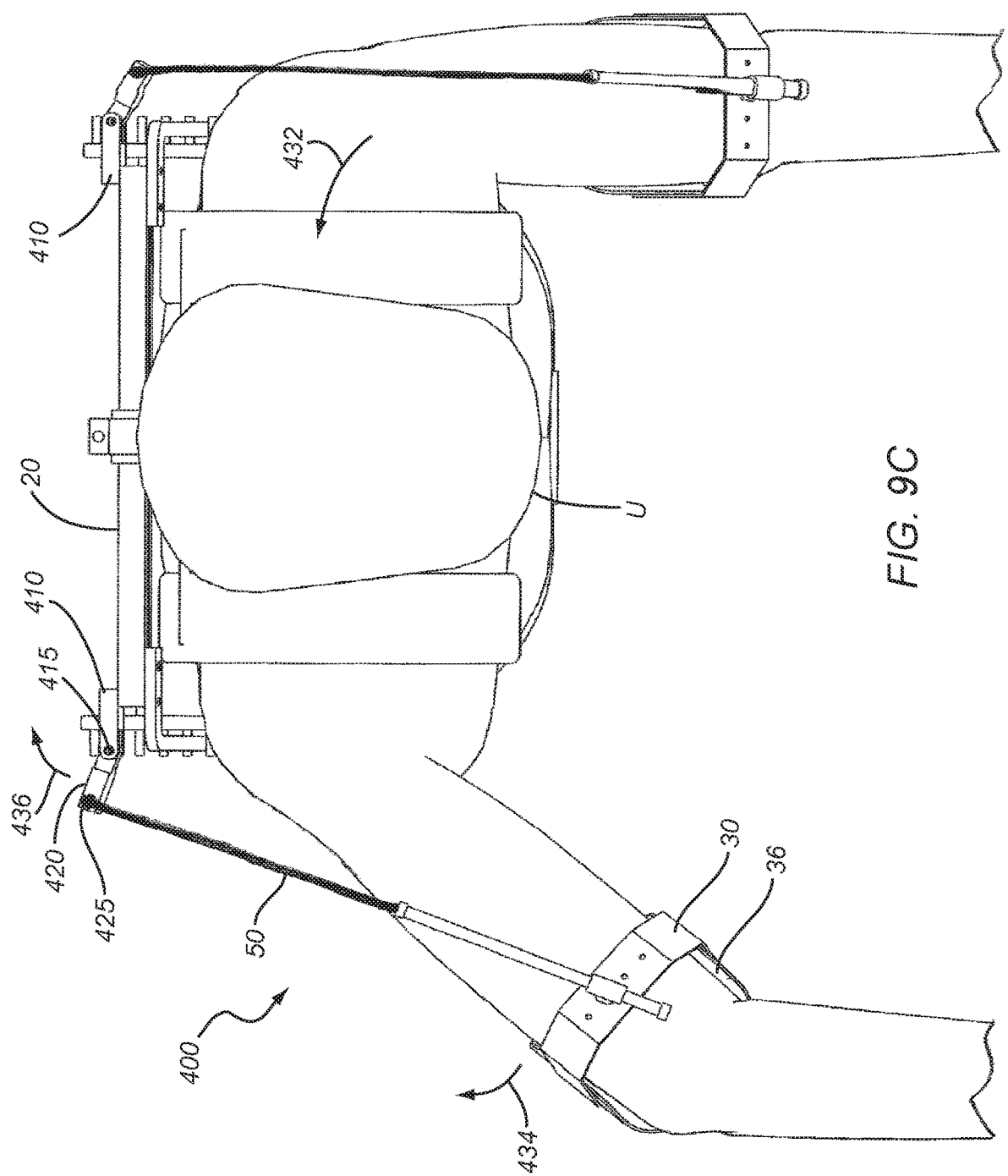
FIG. 9C is a top view of the adaptive arm support system of FIGS. 9A and 9B.

Turning to FIGS. 9A-9C, another exemplary embodiment of an adaptive arm support system 400 is shown worn by a user U. The system 400 is generally similar to other embodiments herein, i.e., including one or more compensation elements (one shown for each arm) 50 coupled between a crossbar 20 of a frame or harness, and an arm bracket 30 and/or arm rest 36 supporting one or both arms of the user U such that the compensation elements 50 pass over the user's shoulders from the cross bar 20 to the arm bracket 30 without contacting the shoulders when worn by the user U. Unlike previous embodiments, the proximal ends of the compensation elements 50 are coupled to hinge components 410, 420, e.g., at anchor point 425, to create pivot point 415. For example, a first hinge component 410 may be fixedly attached to the crossbar 20, and the anchor point 425 of the compensation elements 50 may be fixedly received in or otherwise attached to a second hinge component 420. The hinge components 410, 420 may pivot relative to one another about a single axis 430, as shown, or may pivot about multiple axes or may including a rotational socket allowing rotation in two dimensions (not shown). Thus, the hinge components 410, 420 may permit anchor point 425 to pivot about axis 430 approximately along paths 435 and 436 in response to sideways motion of user's arm approximately along paths 432 and 434.

Turning to FIGS. 10A-10E, another exemplary embodiment of an adaptive arm support system 500 is shown worn by a user U. The system 500 is generally similar to other embodiments herein, i.e., including one or more compensation elements (one shown for each arm) 50 coupled between a crossbar 20 of a frame or harness, and an arm bracket 30 and/or arm rest 36 supporting one or both arms of the user U. Similar to the system 400 of FIGS. 9A-9C, the proximal ends of the compensation elements 50 are coupled to hinge components 510, 520 to create pivot point 512, which may accommodate movement of the user U's arm, e.g., about vertical axis 550 and/or along path 552. For example, a first hinge component 510 may be fixedly attached to the crossbar 20, and a second hinge component 520 may be free to pivot relative to the first hinge component 510 about vertical axis 545, e.g., in response to sideways motion of user's arm approximately along paths 560 and 565.

Unlike the previous embodiment, a lockably rotatable mount 530 is coupled to the second hinge component 520 at distal pivot point 522 such that the rotatable mount 530 may be selectively rotated about axis 570. The proximal ends of the compensation elements 50 may be coupled to the rotatable mount 530, e.g., permanently or removably received in a socket 540 in the rotatable mount 530 similar to other embodiments herein. During use, the rotatable mount 530 may be released, the relative orientation of the rotatable mount 530 with the second hinge component 520 about axis 570 may be adjusted, and then the rotatable mount 530 may be locked again, thereby fixing the relative orientation.

Thus, the proximal ends of the compensation elements 50 may pivot freely about the vertical axis 545, e.g., in response to sideways motion of user's arm approximately along paths 560 and 565, while the rotatable mount 530 may be selectively adjusted and locked. In this configuration, the vertical axis 545 of the hinge components 510, 520 may remain substantially parallel to the vertical axis of the harness, e.g., substantially parallel to the longitudinal axis of the vertical bar 15, unlike the system 400 of FIGS. 9A-9C, in which the vertical axis 430 may not always be parallel to the vertical axis of the harness.

Figure 10A:
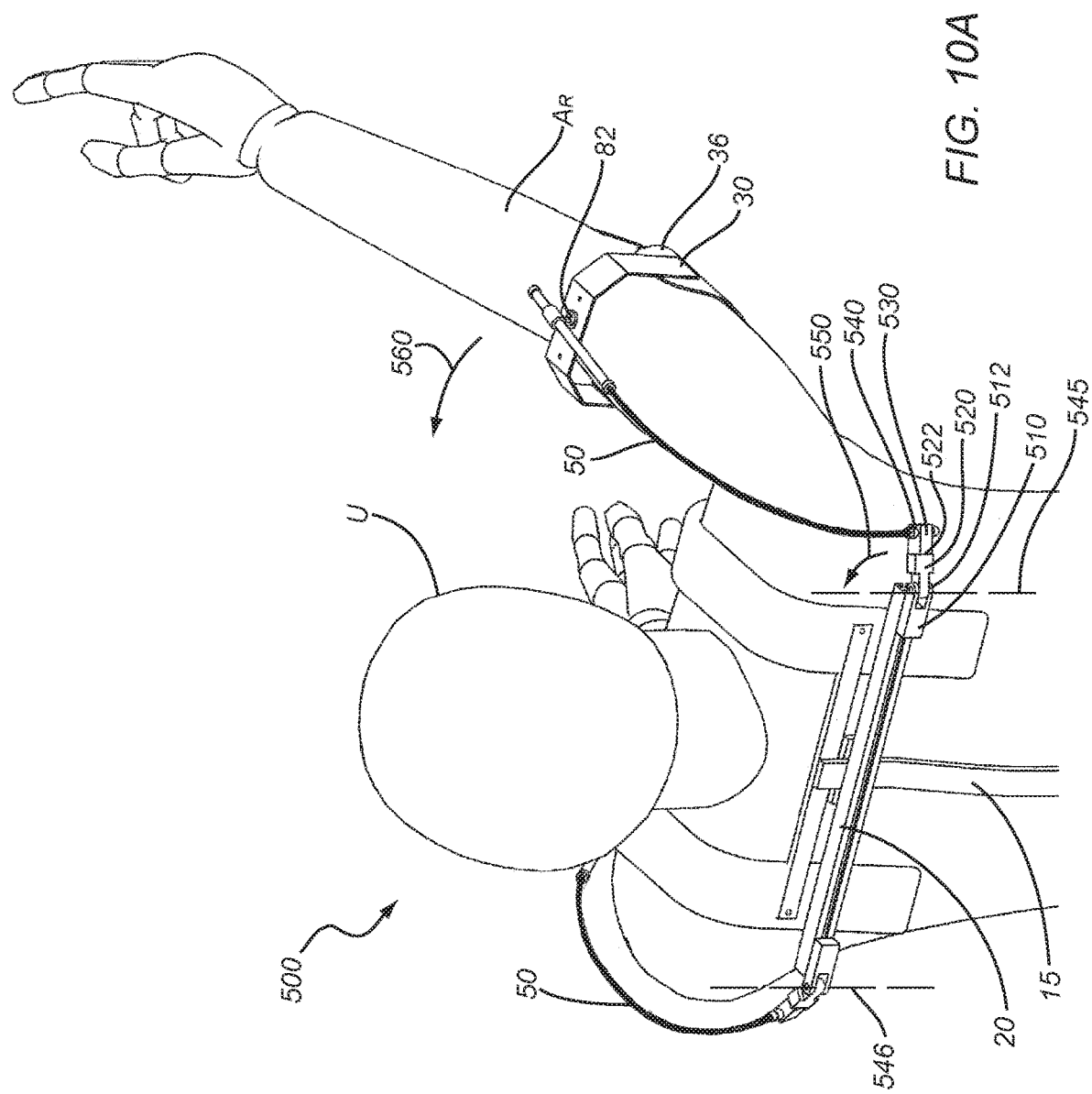
FIGS. 10A and 10B are perspective views of yet another exemplary embodiment of a body-mountable adaptive arm support system worn by a user, showing the user's right arm in different positions.
Figure 10B:
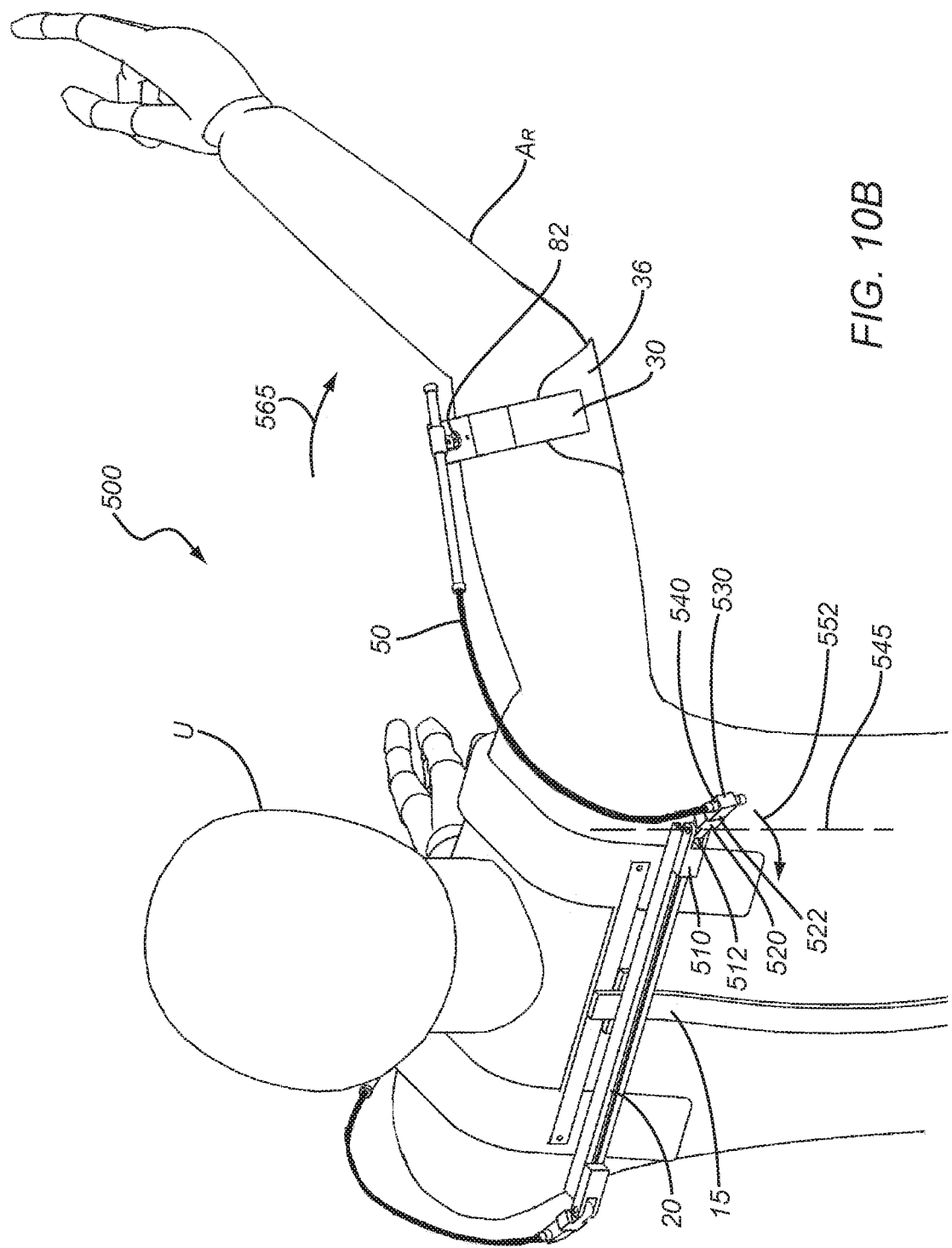
Figure 10D:
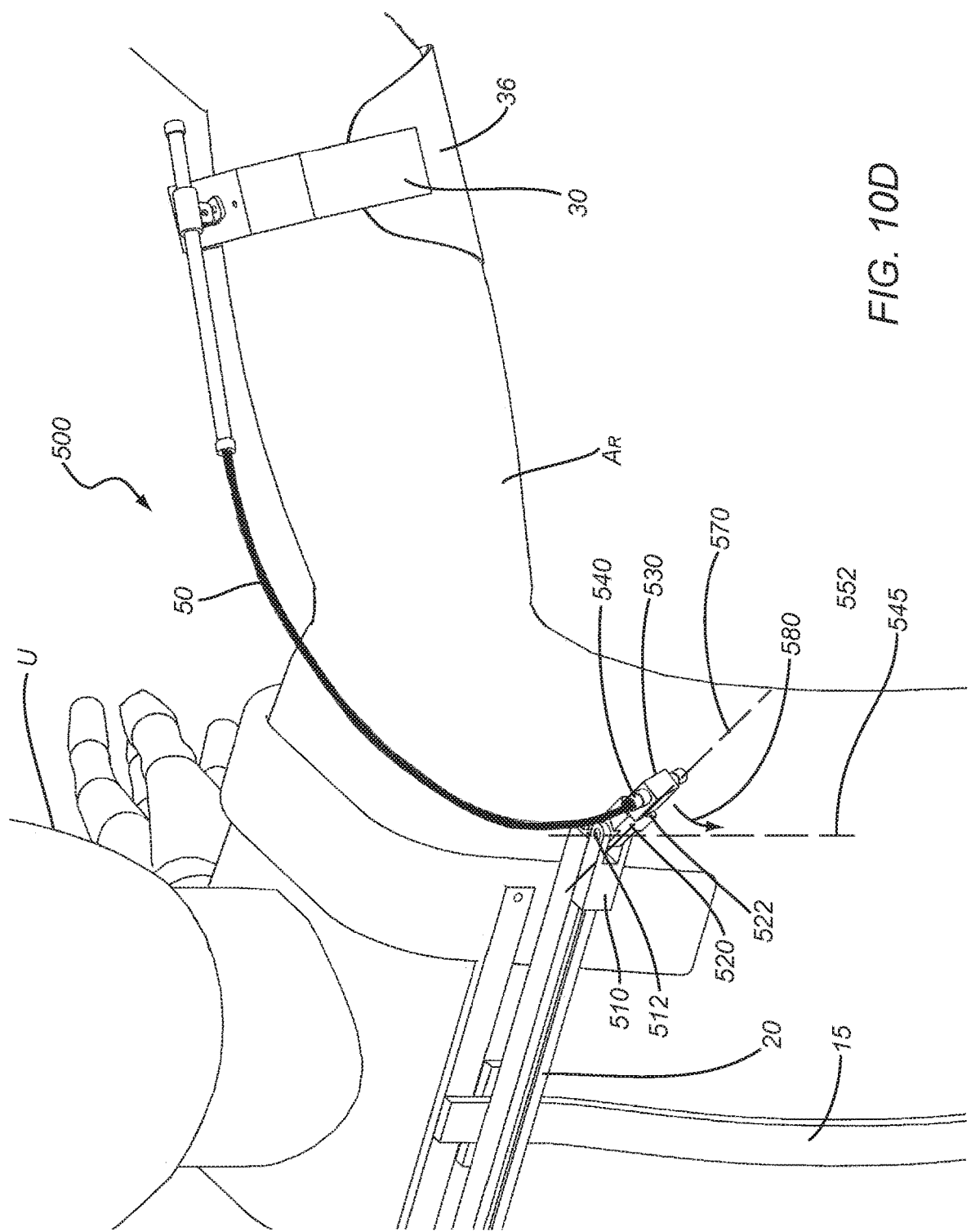
FIGS. 10D and 10E are details of the adaptive arm support system of FIGS. 10A and 10B, showing a rotatable mount thereon in different positions to modify the amount of compensation provided by the system.
Figure 10E:
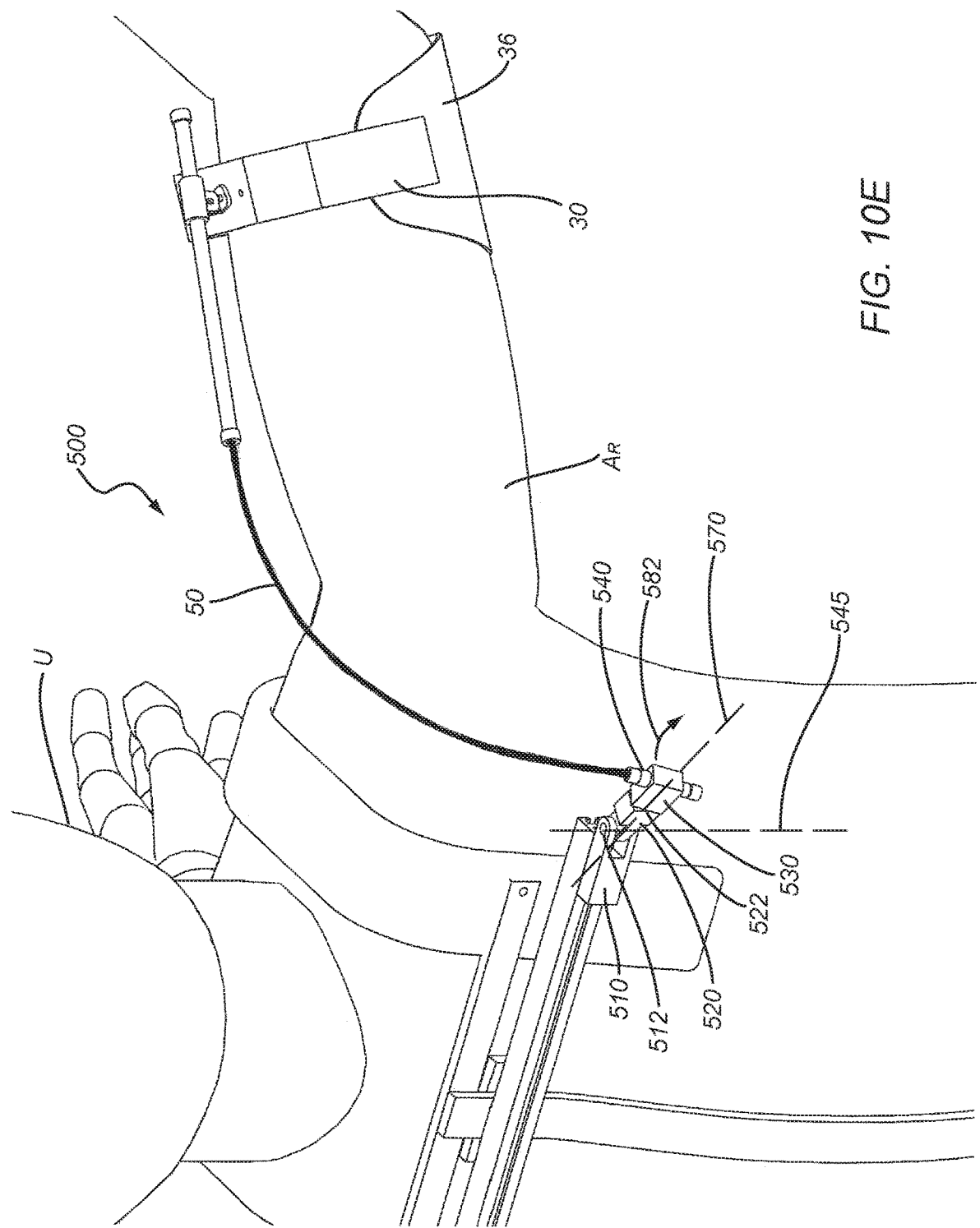

The distal pivot 522 may be used to lockably rotate the rotatable mount 530 relative to hinge components 510, 520 about axis 570, which may change the restoring force on the user U's arm, e.g., adjusting the level of compensation and/or the "zero" point for the system 500. For example, as shown in FIGS. 10B and 10C, the rotatable mount 530 is square with the second hinge component 520. In FIG. 10D, the rotatable mount 530 has been rotatably offset from the second hinge component 520, e.g., approximately along path 580, which may raise the zero point or increase the compensation when the user U's arm is lowered, since the proximal end of the compensation element 50 is offset away from the vertical axis of the harness. Similarly, in FIG. 10E, the rotatable mount 530 has been rotatably offset from the second hinge component 520, e.g., approximately along path 582, which may lower the zero point or decrease the compensation when the user U's arm is lowered.

It will be appreciated that the systems described above may be used in a variety of fields and applications. For example, the systems may be worn by physicians, e.g., surgeons, dentists, and the like, to facilitate extension of the physician's arm(s) during an extended surgical, medical, or dental procedure. The systems may be worn by construction workers, e.g., painters, carpenters, and the like, manufacturing workers, e.g., involved in product assembly, and the like, disabled individuals, and/or other users who perform tasks for an extended period of time in which one or both arms may be extended outwardly from the user's body.

Generally, the devices and systems herein may be worn or otherwise placed on the user's body, e.g., by securing a harness onto the user's abdomen, e.g., their waist, hips, shoulders, back, chest, and the like. An arm support of the devices or systems, e.g., coupled to or otherwise carried by the harness, may be used to support the user's arm such that the arm support subsequently follows movement of the user's arm. The user may then perform one or more tasks involving movement of the user's arm, the arm support at least partially offsetting a gravitational force acting on the user's arm and/or at least partially transferring the gravitational force to the user's abdomen during the movement without substantially interfering in the movement. Thus, the devices and systems herein may facilitate the user performing the task(s) for greater lengths of time and/or with reduced fatigue and/or injury.

It will be appreciated that elements or components shown with any embodiment herein are merely exemplary for the specific embodiment and may be used on or in combination with other embodiments disclosed herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

I claim:

1. A method for supporting an arm of a user during one or more tasks, comprising:
    placing a harness on a torso of the user;
    supporting a portion of the user's arm using an arm support that follows movement of the user's arm and one or more elongate resilient elements coupled between the arm support and the harness; and
    performing one or more tasks involving movement or resting of the user's arm, the one or more elongate resilient elements at least partially offsetting a gravitational force acting on the user's arm during the movement without substantially interfering in the movement,
    wherein the harness comprises a vertical bar extending along a spine of the user wearing the harness, and a cross bar attached to the vertical bar such that a first end of the cross bar is configured to be located behind a shoulder of the user wearing the harness, and wherein a first end of the resilient member is connected to the first end of the cross bar and passes over the shoulder between the cross bar and the arm support without contacting the shoulder, and
    wherein the one or more resilient members are biased to at least partially straighten towards a predetermined orientation, thereby applying a bending restoring force to at least partially offset the gravitational force acting on the user's arm.

2. The method of claim 1, wherein supporting a portion of the user's arm comprises supporting both arms of the user using respective arm supports and two sets of one or more elongate resilient elements coupled between the harness and the pair of arm supports, and wherein performing one or more tasks involves movement of both of the user's arms, the elongate resilient elements at least partially offsetting a gravitational force acting on the respective arm during the movement without substantially interfering in the movement.

3. The method of claim 1, further comprising: selecting one or more of the elongate resilient elements having desired support properties; and coupling the one or more elongate resilient elements between the harness and the arm support.

4. The method of claim 3, wherein two or more of the one or more elongate resilient elements are selected and coupled between the harness and the arm support.

5. The method of claim 3, further comprising wherein selecting one or more of the elongate resilient elements comprises providing a plurality of the elongate resilient elements having different stiffnesses from one another.

6. The method of claim 3, adjusting a connection between the one or more elongate resilient elements and the harness to modify the degree of gravitational force offset by the one or more elongate resilient elements.

7. A method for supporting an appendage of a user during one or more tasks, comprising:
    placing a harness on a torso of the user such that a support bar is located adjacent the user's torso;
    securing a support to the appendage such that an elongate resilient member extends from the support to the support bar; and
    performing one or more tasks involving movement of the appendage, the resilient member biased to a predetermined configuration yet resiliently deflecting to apply a support force acting on the appendage as the user moves to reduce fatigue,
    wherein the support bar comprises a vertical bar extending vertically along the user's back, wherein a first end of the resilient member is coupled to the vertical bar, and wherein a second end of the resilient member is coupled to the support by a slide mount that is movable relative to the second end to accommodate movement of the appendage.

8. The method of claim 7, wherein the appendage is an arm of the user.

9. The method of claim 7, wherein the slide mount is slidable along a length of the second end of the resilient member.

10. The method of claim 7, wherein the slide mount is rotatable around the second end of the resilient member.

11. The method of claim 7, wherein the resilient member is biased to a predetermined configuration yet resiliently deflects to at least partially offset the gravitational force acting on the appendage as the user moves.

12. The method of claim 11, wherein the resilient member is biased to a substantially straight configuration.

13. A method for supporting an appendage of a user during one or more tasks, comprising:
    placing a harness on a torso of the user such that a support bar is located behind the user's back;
    securing a support to the appendage such that an elongate resilient member extends from the support to the support bar, the resilient member coupled to the support by a slide mount that slides along and rotates relative to resilient member to accommodate movement of the appendage; and
    performing one or more tasks involving movement of the appendage, the resilient member applying a support force acting on the user's appendage during the movement to reduce fatigue.

14. The method of claim 13, wherein the resilient member is biased to a predetermined configuration yet resiliently deflects to apply the support force acting on the appendage.

15. The method of claim 14, wherein the resilient member is biased to a substantially straight configuration.

16. The method of claim 13, wherein the support bar comprises a vertical bar extending vertically along the user's back, wherein a first end of the resilient member is coupled to the vertical bar.

17. The method of claim 13, wherein the appendage comprises an arm of the user, and wherein the support force at least partially offsets a gravitational force acting on the user's appendage during the movement.

* * * * *